US010642955B2

(12) United States Patent
Horseman et al.

(10) Patent No.: US 10,642,955 B2
(45) Date of Patent: May 5, 2020

(54) DEVICES, METHODS, AND COMPUTER MEDIUM TO PROVIDE REAL TIME 3D VISUALIZATION BIO-FEEDBACK

(71) Applicant: Saudi Arabian Oil Company, Dhahran (SA)

(72) Inventors: Samantha J. Horseman, Dhahran (SA); Linda Gilligan, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 1150 days.

(21) Appl. No.: 14/959,269

(22) Filed: Dec. 4, 2015

(65) Prior Publication Data

US 2017/0161432 A1    Jun. 8, 2017

(51) Int. Cl.
*G06F 19/00*    (2018.01)
*G06F 3/0484*    (2013.01)
(Continued)

(52) U.S. Cl.
CPC ........ *G06F 19/321* (2013.01); *G06F 3/04815* (2013.01); *G06F 3/04842* (2013.01);
(Continued)

(58) Field of Classification Search
None
See application file for complete search history.

(56) References Cited

U.S. PATENT DOCUMENTS 4,951,963 A    8/1990 Behr et al.
4,998,534 A    3/1991 Claxton, III et al.
(Continued)

FOREIGN PATENT DOCUMENTS

AU    767533 B2    11/2003
CN    101065752 A    10/2007
(Continued)

OTHER PUBLICATIONS

Jamison, Dean T., et al.; "The World Health Report 1999" World Health Organization, WHO Library Cataloguing in Publication Data, 1999; pp. 1-136.
(Continued)

*Primary Examiner* — Devin C Hein
(74) *Attorney, Agent, or Firm* — Bracewell LLP; Constance G. Rhebergen; Christopher L. Drymalla

(57) ABSTRACT

A device to provide three-dimensional (3D) depictions of health of human organs of a user relative to the user's age based on sensed biometrics of the user. The device may comprise one or more processors; one or more databases in communication with the one or more processors and having a plurality of three-dimensional (3D) depictions of each of one or more human organs stored therein. The plurality of 3D depictions of each of the one or more human organs define a set of base images of the respective human organ, each set of base images configured to include a plurality of base images of the respective human organ at each of a plurality of different ages, the plurality of base images of the respective human organ at each of the plurality of different ages configured to include one or more depictions of the respective human organ at the respective different age at each of a plurality of health levels among a range of health levels, each of the plurality of health levels configured to indicate health risk.

19 Claims, 16 Drawing Sheets

(51) Int. Cl.
  *G06F 3/0481* (2013.01)
  *G06T 7/00* (2017.01)
  *G16H 40/63* (2018.01)
  *G16H 50/30* (2018.01)
  *G16H 50/50* (2018.01)
  *G16H 20/70* (2018.01)

(52) U.S. Cl.
  CPC ............ *G06T 7/0016* (2013.01); *G16H 20/70* (2018.01); *G16H 40/63* (2018.01); *G16H 50/30* (2018.01); *G16H 50/50* (2018.01); *G06T 2200/24* (2013.01); *G06T 2207/30004* (2013.01); *G06T 2210/41* (2013.01)

(56) References Cited

U.S. PATENT DOCUMENTS

| | | |
|---|---|---|
| 5,000,188 A | 3/1991 | Kojima |
| 5,111,539 A | 5/1992 | Hiruta et al. |
| 5,253,656 A | 10/1993 | Rincoe et al. |
| 5,304,112 A | 4/1994 | Mrklas et al. |
| 5,305,238 A | 4/1994 | Starr, III |
| 5,323,650 A | 6/1994 | Fullen et al. |
| 5,331,549 A | 7/1994 | Crawford, Jr. |
| 5,343,869 A | 9/1994 | Pross et al. |
| 5,410,471 A | 4/1995 | Alyfuku et al. |
| 5,435,315 A | 7/1995 | McPhee et al. |
| 5,441,047 A | 8/1995 | David |
| 5,542,420 A | 8/1996 | Goldman et al. |
| 5,570,301 A | 10/1996 | Barrus |
| 5,573,269 A | 11/1996 | Gentry et al. |
| 5,626,145 A | 5/1997 | Clapp et al. |
| 5,673,691 A | 10/1997 | Abrams et al. |
| 5,722,418 A * | 3/1998 | Bro .................. G06F 19/3456 600/545 |
| 5,792,047 A | 8/1998 | Coggins |
| 5,813,993 A | 9/1998 | Kaplan et al. |
| 5,926,806 A | 7/1999 | Marshall et al. |
| 5,937,387 A | 8/1999 | Summerell et al. |
| 6,033,344 A | 3/2000 | Trulaske et al. |
| 6,049,281 A | 4/2000 | Osterweil |
| 6,080,106 A | 6/2000 | Lloyd et al. |
| 6,083,156 A | 7/2000 | Lisiecki |
| 6,104,296 A | 8/2000 | Yasuchi et al. |
| 6,148,280 A | 11/2000 | Kramer |
| 6,149,586 A | 11/2000 | Elkind |
| 6,190,314 B1 | 2/2001 | Ark et al. |
| 6,198,394 B1 | 3/2001 | Jacobsen et al. |
| 6,203,495 B1 | 3/2001 | Bardy |
| 6,269,339 B1 | 7/2001 | Silver |
| 6,281,594 B1 | 8/2001 | Sarich |
| 6,291,900 B1 | 9/2001 | Tiemann et al. |
| 6,293,771 B1 | 9/2001 | Haney et al. |
| 6,307,476 B1 | 10/2001 | Smith et al. |
| 6,309,342 B1 | 10/2001 | Blazey et al. |
| 6,334,837 B1 | 1/2002 | Hein et al. |
| 6,345,839 B1 | 2/2002 | Kuboki et al. |
| 6,353,764 B1 | 3/2002 | Imagawa et al. |
| 6,369,337 B1 | 4/2002 | Machiyama |
| 6,381,577 B1 | 4/2002 | Brown |
| 6,383,136 B1 | 5/2002 | Jordan |
| 6,408,263 B1 | 6/2002 | Summers |
| 6,425,862 B1 | 7/2002 | Brown |
| 6,450,530 B1 | 9/2002 | Frasher et al. |
| 6,452,862 B1 | 9/2002 | Tomotani |
| 6,546,286 B2 | 4/2003 | Olson |
| 6,572,558 B2 | 6/2003 | Masakov et al. |
| 6,585,645 B2 | 7/2003 | Hutchinson |
| 6,594,607 B2 | 7/2003 | Lavery |
| 6,646,556 B1 | 11/2003 | Smith et al. |
| 6,648,820 B1 | 11/2003 | Sarel |
| 6,658,572 B1 | 12/2003 | Craig |
| 6,669,286 B2 | 12/2003 | Iusim |
| 6,673,027 B2 | 1/2004 | Fischer |
| 6,675,130 B2 | 1/2004 | Kanevsky et al. |
| 6,692,258 B1 | 2/2004 | Kurzweil et al. |
| 6,705,990 B1 | 3/2004 | Gallant et al. |
| 6,736,642 B2 | 5/2004 | Bajer |
| 6,767,330 B2 | 7/2004 | Lavery et al. |
| 6,768,246 B2 | 7/2004 | Pelrine et al. |
| 6,781,067 B2 | 8/2004 | Montagnino et al. |
| 6,828,908 B2 | 12/2004 | Clark |
| 6,832,987 B2 | 12/2004 | David et al. |
| 6,850,798 B2 | 2/2005 | Morgan |
| 6,918,769 B2 | 7/2005 | Rink |
| 6,931,359 B2 | 8/2005 | Tamada |
| 6,982,497 B2 | 1/2006 | Rome |
| 7,005,757 B2 | 2/2006 | Pandian |
| 7,027,621 B1 | 4/2006 | Prokoski |
| 7,063,665 B2 | 6/2006 | Hasegawa et al. |
| 7,074,198 B2 | 7/2006 | Krullaards |
| 7,104,965 B1 | 9/2006 | Jiang et al. |
| 7,109,872 B2 | 9/2006 | Balaban et al. |
| 7,128,577 B2 | 10/2006 | Renaud |
| 7,152,024 B2 | 12/2006 | Marschner |
| 7,155,158 B1 | 12/2006 | Iuppa |
| 7,163,489 B1 | 1/2007 | Nelson |
| 7,188,151 B2 | 3/2007 | Kumar et al. |
| 7,233,312 B2 | 6/2007 | Stern et al. |
| 7,273,453 B2 | 9/2007 | Shallengerger |
| 7,304,580 B2 | 12/2007 | Sullivan et al. |
| 7,315,249 B2 | 1/2008 | Littell |
| 7,351,206 B2 | 4/2008 | Suzuki |
| 7,399,276 B1 | 7/2008 | Brown et al. |
| 7,407,484 B2 | 8/2008 | Korman |
| 7,481,779 B2 | 1/2009 | Large |
| 7,598,881 B2 | 10/2009 | Morgan |
| 7,624,037 B2 | 11/2009 | Bost |
| 7,652,582 B2 | 1/2010 | Littell |
| 7,689,271 B1 | 3/2010 | Sullivan |
| 7,717,866 B2 | 5/2010 | Damen |
| 7,771,318 B2 | 8/2010 | Narayanaswami |
| 7,830,249 B2 | 11/2010 | Dorneich et al. |
| 7,844,347 B2 | 11/2010 | Brabec |
| 7,849,115 B2 | 12/2010 | Reiner |
| 7,901,324 B2 | 3/2011 | Kodama |
| 7,958,002 B2 | 6/2011 | Bost |
| 7,972,266 B2 | 7/2011 | Gobeyn et al. |
| 7,988,627 B2 | 8/2011 | Bagan |
| 8,015,022 B2 | 9/2011 | Gore |
| 8,018,346 B2 | 9/2011 | Gottleib et al. |
| 8,019,121 B2 | 9/2011 | Marks |
| 8,021,298 B2 | 9/2011 | Baird et al. |
| 8,024,202 B2 | 9/2011 | Carroll |
| 8,030,786 B2 | 10/2011 | Jackson et al. |
| 8,038,615 B2 | 10/2011 | Gobeyn |
| 8,081,083 B2 | 12/2011 | Hinterlong |
| 8,083,676 B2 | 12/2011 | Halliday |
| 8,092,226 B2 | 1/2012 | Findlay |
| 8,095,641 B2 | 1/2012 | Aggarwal et al. |
| 8,103,333 B2 | 1/2012 | Tran |
| 8,179,269 B2 | 5/2012 | Yanagi et al. |
| 8,180,457 B2 | 5/2012 | Matos |
| 8,200,323 B2 | 6/2012 | Dibenedetto et al. |
| 8,203,454 B2 | 6/2012 | Knight et al. |
| 8,219,184 B2 | 7/2012 | Stelzer et al. |
| 8,235,895 B2 | 8/2012 | David |
| 8,308,562 B2 | 11/2012 | Patton |
| 8,359,231 B2 | 1/2013 | Fitzpatrick et al. |
| 8,428,962 B1 | 4/2013 | Brinkley et al. |
| 8,477,039 B2 | 7/2013 | Glecker et al. |
| 8,487,456 B2 | 7/2013 | Donelan et al. |
| 8,597,121 B2 | 12/2013 | Andres Del Valle |
| 8,597,142 B2 | 12/2013 | Mayles et al. |
| 8,612,247 B2 | 12/2013 | Sawano |
| 8,636,670 B2 | 1/2014 | Ferren et al. |
| 8,704,110 B2 | 4/2014 | Forshaw et al. |
| 8,738,129 B2 | 5/2014 | Packer |
| 8,775,196 B2 | 7/2014 | Simpson et al. |
| 8,956,292 B2 | 2/2015 | Wekell et al. |
| 9,043,217 B2 | 5/2015 | Cashman et al. |
| 9,044,172 B2 | 6/2015 | Baxi et al. |
| 9,364,714 B2 | 6/2016 | Koduri et al. |
| 10,169,962 B1 | 1/2019 | Walker et al. |

(56) References Cited

U.S. PATENT DOCUMENTS

| | | |
|---|---|---|
| 2001/0039372 A1 | 11/2001 | Yasushi et al. |
| 2001/0040591 A1 | 11/2001 | Abbott et al. |
| 2001/0041845 A1 | 11/2001 | Kim |
| 2001/0042004 A1 | 11/2001 | Taub |
| 2002/0050924 A1 | 5/2002 | Mahbub |
| 2002/0062069 A1 | 5/2002 | Mault |
| 2002/0077534 A1 | 6/2002 | Durousseau |
| 2002/0087093 A1 | 7/2002 | Chai |
| 2002/0095099 A1 | 7/2002 | Quyen et al. |
| 2002/0108576 A1 | 8/2002 | Lely et al. |
| 2002/0132092 A1 | 9/2002 | Wagner |
| 2002/0156351 A1 | 10/2002 | Sagel |
| 2002/0167486 A1 | 11/2002 | Tan et al. |
| 2002/0183644 A1 | 12/2002 | Levendowski et al. |
| 2002/0193707 A1 | 12/2002 | Atlas et al. |
| 2002/0197591 A1 | 12/2002 | Ebersole et al. |
| 2003/0010345 A1 | 1/2003 | Koblasz et al. |
| 2003/0058111 A1 | 3/2003 | Lee et al. |
| 2003/0060957 A1 | 3/2003 | Okamura et al. |
| 2003/0073552 A1 | 4/2003 | Knight |
| 2003/0109322 A1 | 6/2003 | Funk et al. |
| 2003/0113698 A1 | 6/2003 | Von Der Geest |
| 2003/0149379 A1 | 8/2003 | Krullaards |
| 2003/0154107 A1 | 8/2003 | Medvedeff |
| 2003/0163351 A1 | 8/2003 | Brown et al. |
| 2003/0173120 A1 | 9/2003 | Desrochers et al. |
| 2003/0181830 A1 | 9/2003 | Guimond et al. |
| 2003/0201978 A1 | 10/2003 | Lee et al. |
| 2003/0204130 A1 | 10/2003 | Colston, Jr. et al. |
| 2003/0209113 A1 | 11/2003 | Brooks et al. |
| 2003/0212579 A1 | 11/2003 | Brown et al. |
| 2003/0214408 A1 | 11/2003 | Grajales et al. |
| 2003/0222440 A1 | 12/2003 | Basir |
| 2003/0226695 A1 | 12/2003 | Mault |
| 2004/0002634 A1 | 1/2004 | Nihtila |
| 2004/0004547 A1 | 1/2004 | Appelt et al. |
| 2004/0015191 A1 | 1/2004 | Otman |
| 2004/0095378 A1 | 5/2004 | Vigue |
| 2004/0100283 A1 | 5/2004 | Meyer et al. |
| 2004/0148140 A1 | 7/2004 | Tarassenko et al. |
| 2004/0152956 A1 | 8/2004 | Korman |
| 2004/0162466 A1 | 8/2004 | Quy |
| 2004/0167381 A1 | 8/2004 | Lichter et al. |
| 2004/0193068 A1 | 9/2004 | Burton et al. |
| 2004/0195876 A1 | 10/2004 | Huiban |
| 2004/0214148 A1 | 10/2004 | Salvino et al. |
| 2004/0222892 A1 | 11/2004 | Balaban |
| 2004/0242976 A1 | 12/2004 | Abreu |
| 2004/0260156 A1 | 12/2004 | David |
| 2004/0263633 A1 | 12/2004 | Shinohara et al. |
| 2005/0060217 A1 | 3/2005 | Douglas et al. |
| 2005/0075542 A1 | 4/2005 | Goldreich |
| 2005/0101845 A1 | 5/2005 | Nihtila |
| 2005/0108086 A1 | 5/2005 | Kosman |
| 2005/0113650 A1 | 5/2005 | Pacione et al. |
| 2005/0124864 A1 | 6/2005 | Mack et al. |
| 2005/0164833 A1 | 7/2005 | Florio |
| 2005/0165284 A1 | 7/2005 | Gefen |
| 2005/0181347 A1 | 8/2005 | Barnes |
| 2005/0237385 A1 | 10/2005 | Kosaka et al. |
| 2005/0250996 A1 | 11/2005 | Shirai et al. |
| 2005/0260548 A1 | 11/2005 | Nava |
| 2005/0268401 A1 | 12/2005 | Dixon et al. |
| 2005/0270163 A1 | 12/2005 | Littell |
| 2005/0273890 A1 | 12/2005 | Flaherty et al. |
| 2006/0001545 A1 | 1/2006 | Wolf |
| 2006/0026036 A1 | 2/2006 | Mahmood |
| 2006/0030783 A1 | 2/2006 | Tsai et al. |
| 2006/0047188 A1 | 3/2006 | Bohan |
| 2006/0074708 A1 | 4/2006 | Woods |
| 2006/0090135 A1 | 4/2006 | Fukuda |
| 2006/0122863 A1 | 6/2006 | Gottesman et al. |
| 2006/0135857 A1 | 6/2006 | Ho et al. |
| 2006/0155175 A1 | 7/2006 | Ogino et al. |
| 2006/0183980 A1 | 8/2006 | Yang |
| 2006/0203991 A1 | 9/2006 | Kramer et al. |
| 2006/0240395 A1 | 10/2006 | Faist et al. |
| 2006/0241977 A1 | 10/2006 | Fitzgerald et al. |
| 2006/0253303 A1 | 11/2006 | Brown |
| 2006/0267747 A1 | 11/2006 | Kondo |
| 2006/0287883 A1 | 12/2006 | Turgiss et al. |
| 2007/0004969 A1 | 1/2007 | Kong et al. |
| 2007/0011273 A1 | 1/2007 | Greenstein et al. |
| 2007/0016449 A1 | 1/2007 | Cohen et al. |
| 2007/0017531 A1 | 1/2007 | Large |
| 2007/0038153 A1 | 2/2007 | Basson et al. |
| 2007/0050715 A1 | 3/2007 | Behar |
| 2007/0055185 A1 | 3/2007 | Trandafir et al. |
| 2007/0055549 A1 | 3/2007 | Moore et al. |
| 2007/0083384 A1 | 4/2007 | Geslak et al. |
| 2007/0118398 A1 | 5/2007 | Perls |
| 2007/0136093 A1 | 6/2007 | Rankin |
| 2007/0139362 A1 | 6/2007 | Colton et al. |
| 2007/0146131 A1 | 6/2007 | Boverie |
| 2007/0149360 A1 | 6/2007 | Narayanaswami |
| 2007/0169364 A1 | 7/2007 | Townsend et al. |
| 2007/0179360 A1 | 8/2007 | Mikat |
| 2007/0191727 A1 | 8/2007 | Fadem |
| 2007/0193811 A1 | 8/2007 | Breed et al. |
| 2007/0219419 A1 | 9/2007 | Kenknight et al. |
| 2007/0225118 A1 | 9/2007 | Giorno |
| 2007/0225585 A1 | 9/2007 | Washbon et al. |
| 2007/0244724 A1 | 10/2007 | Pendergast et al. |
| 2007/0256494 A1 | 11/2007 | Nakamura et al. |
| 2007/0270909 A1 | 11/2007 | Saketkhou |
| 2007/0276202 A1 | 11/2007 | Raisanen et al. |
| 2007/0282177 A1 | 12/2007 | Pilz |
| 2007/0296556 A1 | 12/2007 | Wang et al. |
| 2007/0299325 A1 | 12/2007 | Farrell et al. |
| 2008/0001735 A1 | 1/2008 | Tran |
| 2008/0001736 A1 | 1/2008 | Steadman et al. |
| 2008/0052837 A1 | 3/2008 | Blumberg |
| 2008/0077620 A1 | 3/2008 | Gilley et al. |
| 2008/0081963 A1 | 4/2008 | Naghavi et al. |
| 2008/0083416 A1 | 4/2008 | Xia et al. |
| 2008/0015422 A1 | 6/2008 | Wessel |
| 2008/0140140 A1 | 6/2008 | Grimley |
| 2008/0146892 A1 | 6/2008 | Leboeuf et al. |
| 2008/0150889 A1 | 6/2008 | Stern |
| 2008/0161654 A1 | 7/2008 | Teller et al. |
| 2008/0171914 A1 | 7/2008 | Ouwekerk et al. |
| 2008/0177158 A1 | 7/2008 | Teller et al. |
| 2008/0177341 A1 | 7/2008 | Bowers |
| 2008/0177614 A1 | 7/2008 | An et al. |
| 2008/0177836 A1 | 7/2008 | Bennett |
| 2008/0188777 A1 | 8/2008 | Bedziouk |
| 2008/0193905 A1 | 8/2008 | Leung |
| 2008/0194995 A1 | 8/2008 | Grady-Van Den Nieuwboer |
| 2008/0200774 A1 | 8/2008 | Luo |
| 2008/0205693 A1 | 8/2008 | Kitamura et al. |
| 2008/0218331 A1 | 9/2008 | Baillot |
| 2008/0228046 A1 | 9/2008 | Futatsuyama et al. |
| 2008/0242521 A1 | 10/2008 | Einav |
| 2008/0242951 A1 | 10/2008 | Jung et al. |
| 2008/0242952 A1 | 10/2008 | Jung et al. |
| 2008/0258921 A1 | 10/2008 | Woo et al. |
| 2008/0292151 A1 | 11/2008 | Kurtz et al. |
| 2008/0294018 A1 | 11/2008 | Kurtz et al. |
| 2008/0304712 A1 | 12/2008 | Rowe et al. |
| 2008/0306357 A1 | 12/2008 | Korman |
| 2008/0306762 A1 | 12/2008 | James |
| 2009/0002178 A1 | 1/2009 | Guday et al. |
| 2009/0030290 A1 | 1/2009 | Kozuch et al. |
| 2009/0030767 A1 | 1/2009 | Morris et al. |
| 2009/0040196 A1 | 2/2009 | Duckstein |
| 2009/0047644 A1 | 2/2009 | Mensah |
| 2009/0047645 A1 | 2/2009 | Dibenedetto et al. |
| 2009/0055204 A1 | 2/2009 | Pennington et al. |
| 2009/0058661 A1 | 3/2009 | Glecker et al. |
| 2009/0137882 A1 | 5/2009 | Baudino et al. |
| 2009/0149721 A1 | 6/2009 | Yang |
| 2009/0149799 A1 | 6/2009 | Dacey, Jr. et al. |
| 2009/0156888 A1 | 6/2009 | Su et al. |
| 2009/0160640 A1 | 6/2009 | Leung et al. |

(56) References Cited

U.S. PATENT DOCUMENTS

| | | |
|---|---|---|
| 2009/0173549 A1 | 7/2009 | Lev |
| 2009/0177688 A1 | 7/2009 | Karlsen et al. |
| 2009/0178858 A1 | 7/2009 | Daniels et al. |
| 2009/0198521 A1 | 8/2009 | Barker |
| 2009/0209829 A1 | 8/2009 | Yanagidaira et al. |
| 2009/0216558 A1 | 8/2009 | Reisman et al. |
| 2009/0231145 A1 | 9/2009 | Wada et al. |
| 2009/0241177 A1 | 9/2009 | Bluth |
| 2009/0287101 A1 | 11/2009 | Ferren et al. |
| 2009/0287191 A1 | 11/2009 | Ferren |
| 2009/0298025 A1 | 12/2009 | Raber |
| 2009/0300616 A1 | 12/2009 | Sicurello et al. |
| 2009/0307025 A1 | 12/2009 | Menon |
| 2009/0319297 A1 | 12/2009 | Hernandez et al. |
| 2009/0324024 A1 | 12/2009 | Worthington |
| 2010/0010365 A1 | 1/2010 | Terao et al. |
| 2010/0014711 A1 | 1/2010 | Camhi et al. |
| 2010/0049004 A1 | 2/2010 | Edman et al. |
| 2010/0049541 A1 | 2/2010 | Pollard et al. |
| 2010/0063837 A1 | 3/2010 | Bellante et al. |
| 2010/0130808 A1 | 5/2010 | Hattori |
| 2010/0131283 A1 | 5/2010 | Linthicum et al. |
| 2010/0169118 A1 | 7/2010 | Rottsolk et al. |
| 2010/0169219 A1 | 7/2010 | Sellers et al. |
| 2010/0205541 A1 | 8/2010 | Rapaport et al. |
| 2010/0225489 A1 | 9/2010 | Hinterlong |
| 2010/0240458 A1 | 9/2010 | Gaiba et al. |
| 2010/0259043 A1 | 10/2010 | Balsamo |
| 2010/0261978 A1 | 10/2010 | Lithgow |
| 2010/0283265 A1 | 11/2010 | Rastegar et al. |
| 2010/0286567 A1 | 11/2010 | Wolfe et al. |
| 2010/0292545 A1 | 11/2010 | Berka et al. |
| 2010/0293267 A1 | 11/2010 | Ribak et al. |
| 2010/0298656 A1 | 11/2010 | McCombie et al. |
| 2010/0299257 A1 | 11/2010 | Turk |
| 2010/0305480 A1 | 12/2010 | Guoyi et al. |
| 2010/0312606 A1 | 12/2010 | Gala |
| 2010/0332250 A1 | 12/2010 | Simpson |
| 2011/0030838 A1 | 2/2011 | Turiello |
| 2011/0033830 A1 | 2/2011 | Cherian |
| 2011/0035231 A1 | 2/2011 | Firminger et al. |
| 2011/0046688 A1 | 2/2011 | Schwibner |
| 2011/0055720 A1 | 3/2011 | Potter et al. |
| 2011/0060252 A1 | 3/2011 | Simonsen et al. |
| 2011/0080290 A1 | 4/2011 | Baxi et al. |
| 2011/0098056 A1 | 4/2011 | Rhoads et al. |
| 2011/0119075 A1 | 5/2011 | Dhoble |
| 2011/0125662 A1 | 5/2011 | Perry et al. |
| 2011/0137211 A1 | 6/2011 | Weisberg |
| 2011/0137669 A1 | 6/2011 | Bennett |
| 2011/0152635 A1 | 6/2011 | Morris et al. |
| 2011/0152696 A1 | 6/2011 | Ryan |
| 2011/0161100 A1 | 6/2011 | Peak et al. |
| 2011/0172744 A1 | 7/2011 | Davis et al. |
| 2011/0183305 A1 | 7/2011 | Orbach |
| 2011/0196212 A1 | 8/2011 | Peters et al. |
| 2011/0201960 A1 | 8/2011 | Price |
| 2011/0213664 A1 | 9/2011 | Osterhout et al. |
| 2011/0238591 A1 | 9/2011 | Kerr et al. |
| 2011/0257537 A1 | 10/2011 | Alatriste |
| 2011/0269601 A1 | 11/2011 | Nelson et al. |
| 2011/0270135 A1 | 11/2011 | Dooley et al. |
| 2011/0275939 A1 | 11/2011 | Walsh et al. |
| 2011/0285146 A1 | 11/2011 | Kozinsky et al. |
| 2011/0295466 A1 | 12/2011 | Ostu et al. |
| 2011/0295656 A1 | 12/2011 | Venkatasubramanian et al. |
| 2012/0007367 A1 | 1/2012 | Chang |
| 2012/0010488 A1 | 1/2012 | Henry et al. |
| 2012/0035433 A1 | 2/2012 | Chance |
| 2012/0040799 A1 | 2/2012 | Jaquish et al. |
| 2012/0052971 A1 | 3/2012 | Bentley |
| 2012/0071731 A1 | 3/2012 | Gottesman |
| 2012/0075483 A1 | 3/2012 | Paoletti |
| 2012/0086249 A1 | 4/2012 | Hotary et al. |
| 2012/0117020 A1 | 5/2012 | Davis et al. |
| 2012/0122430 A1 | 5/2012 | Hutchings et al. |
| 2012/0127157 A1 | 5/2012 | Adler et al. |
| 2012/0130196 A1 | 5/2012 | Jain et al. |
| 2012/0139731 A1 | 6/2012 | Razoumov et al. |
| 2012/0143031 A1 | 6/2012 | Belalcazar et al. |
| 2012/0143374 A1 | 6/2012 | Mistry et al. |
| 2012/0146795 A1 | 6/2012 | Margon et al. |
| 2012/0154277 A1 | 6/2012 | Bar-Zeev et al. |
| 2012/0203465 A1 | 8/2012 | Callewaert et al. |
| 2012/0203491 A1 | 8/2012 | Sun et al. |
| 2012/0209563 A1 | 8/2012 | Takeda et al. |
| 2012/0215076 A1 | 8/2012 | Yang et al. |
| 2012/0215976 A1 | 8/2012 | Inoue |
| 2012/0253484 A1 | 10/2012 | Burich et al. |
| 2012/0271121 A1 | 10/2012 | Della Torre et al. |
| 2012/0271143 A1 | 10/2012 | Aragones et al. |
| 2012/0283929 A1 | 11/2012 | Wakita et al. |
| 2012/0289793 A1 | 11/2012 | Jain et al. |
| 2012/0290215 A1 | 11/2012 | Adler et al. |
| 2012/0302910 A1 | 11/2012 | Freeman et al. |
| 2012/0323590 A1 | 12/2012 | Udani |
| 2013/0009761 A1 | 1/2013 | Horseman |
| 2013/0009993 A1 | 1/2013 | Horseman |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0013327 A1 | 1/2013 | Horseman |
| 2013/0013331 A1 | 1/2013 | Horseman |
| 2013/0056981 A1 | 3/2013 | Mullins et al. |
| 2013/0097093 A1 | 4/2013 | Kolber et al. |
| 2013/0158423 A1 | 6/2013 | Kapoor |
| 2013/0178960 A1 | 7/2013 | Sheehan et al. |
| 2013/0217350 A1 | 8/2013 | Singh |
| 2013/0226413 A1 | 8/2013 | Cuddihy et al. |
| 2013/0234826 A1 | 9/2013 | Sekiguchi et al. |
| 2013/0243208 A1 | 9/2013 | Fawer |
| 2013/0281798 A1 | 10/2013 | Rau et al. |
| 2013/0282609 A1 | 10/2013 | Au et al. |
| 2013/0289889 A1 | 10/2013 | Yuen et al. |
| 2013/0297219 A1 | 11/2013 | Bangera et al. |
| 2013/0297344 A1 | 11/2013 | Cosentino et al. |
| 2013/0308099 A1 | 11/2013 | Stack |
| 2013/0331993 A1 | 12/2013 | Detsch et al. |
| 2013/0334851 A1 | 12/2013 | Hoell et al. |
| 2014/0041105 A1 | 2/2014 | Zemlak |
| 2014/0067001 A1 | 3/2014 | Schwibner et al. |
| 2014/0100464 A1 | 4/2014 | Kaleal et al. |
| 2014/0107718 A1 | 4/2014 | Foote |
| 2014/0129401 A1 | 5/2014 | Kruz et al. |
| 2014/0156259 A1 | 6/2014 | Dolan et al. |
| 2014/0172461 A1 | 6/2014 | Rogers |
| 2014/0222095 A1 | 8/2014 | Einy |
| 2014/0304020 A1 | 10/2014 | Casper |
| 2014/0317914 A1 | 10/2014 | Shaker |
| 2014/0372133 A1 | 12/2014 | Austrum et al. |
| 2015/0025928 A1 | 1/2015 | Kang et al. |
| 2015/0050623 A1 | 2/2015 | Falash et al. |
| 2015/0134347 A1* | 5/2015 | Faurie .................. G06Q 50/22 |
| | | 705/2 |
| 2015/0199494 A1 | 7/2015 | Koduri et al. |
| 2015/0222096 A1 | 8/2015 | Nakayama |
| 2015/0338265 A1 | 11/2015 | Carreel et al. |
| 2015/0375028 A1 | 12/2015 | Oteman et al. |
| 2016/0132046 A1 | 5/2016 | Beoughter et al. |
| 2016/0321935 A1* | 11/2016 | Mohler .................. G09B 5/08 |
| 2017/0245806 A1 | 8/2017 | Elhawary et al. |
| 2017/0290516 A1* | 10/2017 | Nguyen ................ G16H 50/30 |

FOREIGN PATENT DOCUMENTS

| | | |
|---|---|---|
| CN | 101115438 A | 1/2008 |
| CN | 201127606 Y | 10/2008 |
| CN | 101454050 A | 6/2009 |
| CN | 101930125 A | 12/2010 |
| DE | 102005048496 A1 | 4/2007 |

(56) References Cited

FOREIGN PATENT DOCUMENTS

| | | |
|---|---|---|
| EP | 1407713 B1 | 9/2008 |
| EP | 2151355 A1 | 2/2010 |
| EP | 2248461 A2 | 11/2010 |
| EP | 2924674 A1 | 9/2015 |
| JP | 05-049603 A | 3/1993 |
| JP | H07204168 A | 8/1995 |
| JP | H10283150 A | 10/1998 |
| JP | H10312241 A | 11/1998 |
| JP | H11328593 A | 11/1999 |
| JP | 2000037357 A | 2/2000 |
| JP | 2000342537 A | 12/2000 |
| JP | 2001187030 A | 7/2001 |
| JP | 2001209717 A | 8/2001 |
| JP | 2001236141 A | 8/2001 |
| JP | 2001356849 A | 12/2001 |
| JP | 2002065630 A | 3/2002 |
| JP | 2002109061 A | 4/2002 |
| JP | 2002159052 A | 5/2002 |
| JP | 2002183647 A | 6/2002 |
| JP | 2002215880 A | 8/2002 |
| JP | 2002259120 A | 9/2002 |
| JP | 2002291952 A | 10/2002 |
| JP | 2003070774 A | 3/2003 |
| JP | 2003091598 A | 3/2003 |
| JP | 2003521972 A | 7/2003 |
| JP | 2003235813 A | 8/2003 |
| JP | 2003247991 A | 9/2003 |
| JP | 2003256578 A | 9/2003 |
| JP | 2003310580 A | 11/2003 |
| JP | 2004113581 A | 4/2004 |
| JP | 2004135829 A | 5/2004 |
| JP | 3109753 U | 6/2005 |
| JP | 2005287688 A | 10/2005 |
| JP | 2005321869 A | 11/2005 |
| JP | 2006085262 A | 3/2006 |
| JP | 2006106952 A | 4/2006 |
| JP | 2006178805 A | 7/2006 |
| JP | 2006239157 A | 9/2006 |
| JP | 2008099834 A | 1/2008 |
| JP | 2008110032 A | 5/2008 |
| JP | 2008178546 A | 8/2008 |
| JP | 2008230366 A | 10/2008 |
| JP | 2008264188 A | 11/2008 |
| JP | 2008304978 A | 12/2008 |
| JP | 2009171544 A | 7/2009 |
| JP | 2009532072 A | 9/2009 |
| JP | 2009301360 A | 12/2009 |
| JP | 2010003070 A | 1/2010 |
| JP | 2010181324 A | 8/2010 |
| JP | 2010538701 A | 12/2010 |
| JP | 2011067708 A | 4/2011 |
| JP | 2011120787 A | 6/2011 |
| JP | 2011123579 A | 6/2011 |
| WO | 9601585 A1 | 1/1996 |
| WO | 2001028416 A1 | 4/2001 |
| WO | 2001086403 A2 | 11/2001 |
| WO | 03077110 A2 | 9/2003 |
| WO | 2005064447 A2 | 7/2005 |
| WO | 2006022465 A2 | 3/2006 |
| WO | 2007016056 A2 | 2/2007 |
| WO | 2007130591 A2 | 11/2007 |
| WO | 2008044325 A1 | 4/2008 |
| WO | 2010048145 A1 | 4/2010 |
| WO | 2010051037 A1 | 5/2010 |
| WO | 2010067275 A1 | 6/2010 |
| WO | 2011020299 A1 | 2/2011 |
| WO | WO2014023422 A1 | 2/2014 |

OTHER PUBLICATIONS

Centers for Medicare & Medicaid Services; "National Health Expenditure Data" CMS.gov, available as of May 27, 2016 at: https://www.cms.gov/Research-Statistics-Data-and-Systems/Statistics-Trends-and-Reports/NationalHealthExpendData/index.html; pp. 1-2.

Aldana, Steven G.; "Financial Impact of Health Promotion Programs: A Comprehensive Review of the Literature" American Journal of Health Promotion, May/Jun. 2001, vol. 15, No. 5; pp. 296-320.

Aldana, Steven G., et al.; "Financial impact of a comprehensive multisite workplace health promotion program" Preventive Medicine 40 (2005); pp. 131-137.

Baicker, Katherine, et al.; "Workplace Wellness Programs Can Generate Savings" Health Affairs, 29, No. 2 (2010); pp. 1-9.

Berry, Leonard L., et al.; "What's the Hard Return on Employee Wellness Programs?" Harvard Business Review, Dec. 2010; pp. 104-112.

CDC; "Chronic Diseases and Health Promotion" Centers for Disease Control and Prevention; available as of Dec. 18, 2013 at www.cdc.gov/chronicdisease/overview; pp. 1-3.

Chapman, Larry S.; "Expert Opinions on "Best Practices" in Worksite Health Promotion (WHP)" The Art of Health Promotion, Jul./Aug. 2004; pp. 1-13.

Chapman, Larry S.; "Meta-Evaluation of Worksite Health Promotion Economic Return Studies: 2005 Update" The Art of Health Promotion, Jul./Aug. 200; pp. 1-10.

Chapman, Larry S.; "Meta-Evaluation of Worksite Health Promotion Economic Return Studies: 2012 Update" The Art of Health Promotion, Mar./Apr. 2012; pp. 1-12.

Edington, Dee W.; "Emerging Research: A View From One Research Center" American Journal of Health Promotion, May/Jun. 2001, vol. 15, No. 5; pp. 341-349.

Edington, Marilyn, et al.; "The UAW-GM Health Promotion Program: Successful Outcomes" AAHON Journal, Jan. 2002, vol. 50, No. 1; pp. 26-31.

Goetzel, Ron Z., et al.; "The Relationship Between Modifiable Health Risks and Health Care Expenditures: An Analysis of the Multi-Employer HERO Health Risk and Cost Database" American College of Occupational and Environmental Medicine; Lippincott Williams & Wilkins, 2014; pp. 1-29.

Goetzel, Ron Z., et al.; "Estimating the Return-on-Investment From Changes in Employee Health Risks on The Dow Chemical Company's Health Care Costs" JOEM vol. 47, No. 8, Aug. 2005; pp. 759-768.

Goetzel, Ron Z., et al.; "Health, Absence, Disability, and Presenteeism Cost Estimates of Certain Physical and Mental Health Conditions Affecting U.S. Employers" JOEM vol. 46, No. 4, Apr. 2004; pp. 398-412.

Goetzel, Ron Z., et al.; "The Health and Productivity Cost Burden of the "Top 10" Physical and Mental Health conditions Affecting Six Large U.S. Employers in 1999" JOEM vol. 45, No. 1, Jan. 2003; pp. 5-14.

Hemp, Paul; "Presenteeism: At Work—But Out of It" Harvard Business Review, Oct. 2004; pp. 1-20.

Horseman, Samantha; "Healthy Human Capital as a Business Strategy: The Saudi Aramco Wellness Program (SAWP)" American College of Safety Engineers, ASSE-MEC-2010-22, pp. 178-185.

Horseman, Samantha; "ErgoWELL—An Integrative Strategy" SPE 152629, Society of Petroleum Engineers, SPE Middle East Health, Safety, Security, and Environment Conference and Exhibition, Abu Dhabi, Apr. 2-4, 2012; pp. 1-17.

Johns, Gary; "Presenteeism in the workplace: A review and research agenda" Journal of Organizational Behavior, J. Organiz. Behav. 31, (2010); pp. 519-542.

Riedel, John E., et al.; "The Effect of Disease Prevention and Health Promotion on Workplace Productivity: A Literature Review" American Journal of Health Promotion, Jan./Feb. 2001, vol. 15, No. 3; pp. 167-191.

Roberts, Rosebud O., et al.; "Comparison of Self-Reported and Medical Record Health Care Utilization Measures" Journal of Clinical Epidemiology vol. 49, No. 9, 1996; pp. 989-995.

Sullivan, Sean; "Making the Business Case for Health and Productivity Management" JOEM vol. 46, No. 6 suppl, Jun. 2004; pp. S56-S61.

World Health Organization "Chronicle of The World Health Organization" vol. 1, 1947; pp. 1-202.

(56) References Cited

OTHER PUBLICATIONS

Kymissis et al. "Parasitic Power Harvesting in Shoes" Digest of Papers, Second International Symposium on Wearable Computers, Pittsburgh, PA, Oct. 19-20, 1998, pp. 132-139, XP032385438.
Lamkin, Paul; "The best VR headsets: Oculust Rift, PlayStation VR, Gear VR, HTC Vive . . . virtual reality is back baby" 10 Sep. 16, 2015; available as of Oct. 21, 2015 at the website: http://www.wearable.com/headgear/the-best-ar-and-vrheadsets;pp. 1-1.
Marois, René, and Jason Ivanoff. "Capacity limits of information processing in the brain." Trends in cognitive sciences 9.6 (2005): 296-305.
Moreno, Roxana, and Alfred Valdez. "Cognitive load and learning effects of having students organize pictures and words in multimedia environments: The role of student interactivity and feedback." Educational Technology Research and Development 53.3 (2005).
Moreno, Roxana, and Richard Mayer. "Interactive multimodal learning environments." Educational Psychology Review 19.3 (2007): 309-326.
Moreno, Roxana. "Learning in high-tech and multimedia environments." Current directions in psychological science 15.2 (2006): 63-67.
Myatt, Mike, "The #1 Reason Leadership Development Fails" Forbes, Dec. 19, 2012; available as of Dec. 13, 2015 at the website: http://www.forbes.com/sites/mikemyatt/2012/12/19/the-1-reason-leadership-development-fails/#7e53fcd834ce; pp.
Nintendo of America Inc., Wii Balance Board Operations Manual, 2008, pp. 1-10.
Nintendo of America Inc., Wii Fit Instruction Booklet, 2008, pp. 1-28.
Nintendo Wii Fit, https://www.youtube.com/watch?v=-Taruqvk30E, May 11, 2008.
Ovans, Andrea; "What Resilience Means, and Why it Matters" Harvard Business Review Jan. 5, 2015; pp. 1-6.
Priya, S., "Advances in Energy Harvesting Using Low Profile Piezoelectric Transducers", Materials Science & Engineering, Springer, Mar. 2007, pp. 165-182.
Prochaska et al. 'The Well-Being Assessment for Productivity'—J Occup Environ Med. (JOEM) vol. 53, No. 7, dated Jul. 2011; pp. 735-768.
Qlik Technology Partners available as of Oct. 21, 2015 at the website: http://www.qlik.com/us/partners/technologypartners;pp. 1-21.
Quick, James Campbell, et al. "Executive health: Building strength, managing risks" Academy of Management Executive, May 2000, vol. 14, No. 2, pp. 33-45.
Rao, Leena; "Backed by Google Ventures and Eric Schmidt, Urban Engines Wants to Solve Urban Congestion Using Data Intelligence" available as of Oct. 2, 2015 at the website: http://www.techcrunch.com/2014/05/15/backed-by-google-entures-and-eric-schmidt-urban.
Raybourn, Elaine M., et al. "Adaptive thinking & leadership simulation game training for special forces officers." ITSEC 2005 Proceedings, Interservice/Industry Training, Simulation and Education Conference Proceedings, Nov. 2005.
Ready, Douglas A., et al.; "Are You a High Potential?" Harvard Business Review Jun. 2010; pp. 1-13.
Rimor, Rikki, Yigal Rosen, and Kefaya Naser. "Complexity of social interactions in collaborative learning: The case of online database environment." Interdisciplinary Journal of E-Learning and Learning Objects 6.1 (2010): 355-365.
Rosen, Yigal. "The effects of an animation-based on-line learning environment on transfer of knowledge and on motivation for science and technology learning." Journal of Educational Computing Research 40.4 (2009): 451-467.
Seligman, Martin E.P., "Building Resilience" Harvard Business Review from the Apr. 2011 issue; available as of Dec. 13, 2015 at the website: https://hbr.org/2011/04/building-resilience; pp. 1-15.
Simmonds, Bethany, et al. "Objectively assessed physical activity and subsequent health service use of UK adults aged 70 and over: A four to five year follow up study." PloS one 9.5 (2014): e97676.
Slater et al., "Taking Steps: The Influence of a Walking Technique on Presence in Virtual Reality", ACM Transactions on Computer-Human Interaction, Sep. 1995, pp. 201-219, vol. 2 No. 3.
Spisak, Brian R., et al., "A face for all seasons: Searching for context-specific leadership traits and discovering a general preference for perceived health" Frontiers in Human Neuroscience; Nov. 5, 2014.
The American Heritage Dictionary of the English Language, definition of planar, 2000.
Veeva Systems and Zinc Ahead Join Forces available as of Oct. 2, 2015 at the website: http://www.veeva.com; pp. 1-6.
Wang, Xiaoning. "An Empirical Study of Optimizing Cognitive Load in Multimedia Integrated English Teaching." Studies in Literature and Language 9.3 (2014): 70.
Withings, The Internet connected Body Scale, retrieved with the Wayback Machine using link at www.withings.com, Jan. 11, 2010.
World Economic Forum 'The Workplace Wellness Alliance-Making the Right Investment: Employee Health and the Power of Metrics' dated Jan. 2013; pp. 1-35.
Anonymous: "Automated analyser"—Wikipedia, Jan. 16, 2015; https: ex.php?title=Automated_analyser&oldid=642687889 retrieved on Feb. 8, 2017; XP055343828 (pp. 1-4).
Hacker, et al. "Representation and visualization of variability in a 3D anatomical atlas using the kidney as an example." Medical Imaging. International Society for Optics and Photonics, 2006. XP055342027 (pp. 1-7).
International Search Report and Written Opinion for International Application No. PCT/US2016/064518; International Filing Date Dec. 2, 2016; Report dated Feb. 17, 2017; (pp. 1-16).
International Search Report and Written Opinion for International Application No. PCT/US2016/065042; International Filing Date Dec. 6, 2016; Report dated Mar. 17, 2017; pp. 1-15.
International Search Report and Written Opinion for International PCT application PCT/US2016/064520; International Filing Date Dec. 2, 2016; Report dated Mar. 27, 2017; pp. 1-10.
International Search Report and Written Opinion for International PCT application PCT/US2016/064521; International Filing Date Dec. 2, 2016; Report dated Mar. 20, 2017; pp. 1-17.
Stephens: "I am 38. My heart is only 33, but my lungs are aged 52. Why?" Mail Online; http://www. dailymail.co.uk/health/article-1249009/I-38-My-heart-only33-lungs-aged-52-Why.html; retrieved on Feb. 3, 2017; XP055342045 (pp. 1-7).
Agarabi, Mina, et al., "A sEMG-based Method for Assessing the Design of Computer Mice" 26th Annual International Conference of the IEEE EMBS, Sep. 1-5, 2004; pp. 2450-2453.
Robertini, Nadia, et al., "Capture of Arm-Muscle Deformations using a Depth-Camera" 10 European Conference on Visual Media Production, London, UK, Nov. 6-7, 2013; pp. 1-10.
"40 Best Companies for Leaders—2014" Chief Executive, available as of Dec. 13, 2015 at the website: http://chiefexecutive.net/40-best-companies-for-leaders-2014/; pp. 1-3.
"Augmented Reality", retrieved from <http://en.wikipedia.org/wiki/Augmented_reality>, May 30, 2012. pp. (1-18).
"Biofeedback—MayoClinic_com", retrieved from <http://www.mayoclinic.com/health/biofeedback/MY01072>, May 7, 2012. (pp. 1-2).
"Cardinus Risk Management | Ergonomic & DSE Risk Assessments", retrieved from <http://www.cardinus.com/>, Sep. 12, 2012. (pp. 1-2).
"Clever toilet checks on your health", retrieved from <http://articles.cnn.com/2005-06-28/tech/spark.toilet_1_toilet-toto-bathroom?_s=PM:TECH>, Jun. 28, 2005. (pp. 1-2).
"Electroencephalography (EEG)", retrieved from <http://www.emedicinehealth.com/script/main/art.asp?articlekey-59319&pf=3&page=1>, Jun. 11, 2012. (pp. 1-4).
"Emotiv|EEG System|Electroencephalography", retrieved from <www.emotiv.com/index.asp>, Jun. 11, 2012. (pp. 1-2).
"EmotivEPOC Software Devlopment Kit", retrieved from <www.emotiv.com/store/hardware/epoc-bci-eeg/developer-neuroheadset/>, Jun. 11, 2012. (pp. 1-2).
"Kinect—Xbox.com", retrieved from <http://www.xbox.com/en-US/kinect>, Jun. 11, 2012. (pp. 1-3).

(56) References Cited

OTHER PUBLICATIONS

"Making a Difference", World Health Organisation, Geneva: WHO, 1999, pp. 1-136.
"MomToBe: The Pregnancy Assistant 3.0", retreved from <http://3d2f.com/programs/4-230-momtobe-the-pregnancy-assistant-download.shtml>, Jun. 11, 2012. (pp. 1-2).
"Murray Hill, WellMed Team to Offer Next Generation Online Preventive Health Services" ProQuest, PR Newswire, New York, Nov. 3, 1999, 3 pages.
"Office Athlete Software Prevents Common Repetitive Stress Injuries", retrieved from <http://www.officeathlete.com/>, Sep. 14, 2012. (pp. 1-2).
"OSHA Ergonomic Solutions: Computer Workstations eTool—Checklists", retrieved from <www.osha.gov/SLTC/etools/computerworkstations/checklist.html>, Jun. 11, 2012. (pp. 1-5).
"OSHA Ergonomic Solutions: Computer Workstations eTool—Good Working Positions", retrieved from <www.osha.gov/SLTC/etools/computerworkstations/positions.html>, Jun. 11, 2012. (pp. 1-2).
"OSHA Ergonomic Solutions: Computer Workstations eTool—Work Process and Recognition", retrieved from <www.osha.gov/SLTC/etools/computerworkstations/Workprocess.html>, Jun. 11, 2012. (pp. 1-2).
"OSHA Ergonomic Solutions: Computer Workstations eTool—Workstation Environment", retrieved from <www.osha.gov/SLTC/etools/computerworkstations/wkstation_enviro.html>, Jun. 11, 2012. (pp. 1-3).
"OSHA Ergonomic Solutions: Computer Workstations eTool—Workstations eTool", retrieved from <www.osha.gov/SLTC/etools/computerworkstations/index.html>, Jun. 11, 2012. (p. 1).
"Philips Research—Download Pictures", retrieved from <http://www.research.philips.com/downloads/pictures/healthcare-personal.html>, May 7, 2012. (pp. 1-2).
"Philips Research Technology Backgrounder—MyHeart project", retrieved from <http://www.research.philips.com/technologies/heartcycle/myheart-gen.html>, May 7, 2012. (pp. 1-3).
"Piezo Electric Energy Harvester", Mide Technology Corporation, retrieved Nov. 18, 2013, pp. 1-2.
"Research programs—Philips Research", retrieved from <http://www.research.philips.com/programs/index.html>, May 1, 2012. (pp. 1-2).
"RJL Systems, Products", retrieved from <http://www.rjlsystems.com/products.shtml>, May 7, 2012. (p. 1).
"Signal Conditioning Piezoelectric Sensors", (PDF) Texas Instruments, Application Report SLOA033A, Sep. 2000, pp. 1-6.
"SmartHeart SE102 Heart Rate Monitor", retrieved from <http://us.oregonscientific.com/cat-Sports-and-Health-sub-Heart-Rate-Monitors-prod-SmartHeart-SE102-Heart-Rate-Monitor.html>, May 7, 2012. (pp. 1-4).
"Speedy Assessment | Chiropractic Assessment and Patient Education", retrieved from <http://speedyassessment.com/>, May 7, 2012. (pp. 1-3).
"Stress Thermometer", retrieved from <http://www.biof.com/onlinestore/stressthermometer.asp?redirect=yes>, May 7, 2012. (pp. 1-4).
"The Wellness Imperative, Creating More Effective Organizations", World Economic Forum, 2010. (pp. 1-20).
"Wireless measurement devices—Philips", retreved from <http://www.healthcare.philips.com/us_en/products/telehealth/Products/devices.wpd>, May 7, 2012. (pp. 1-2).
"WorkPace : RSI Injury Prevention Software, Stretch Break Exercise Reminder Software", retrieved from <http://www.workpace.com/>, Sep. 14, 2012. (p. 1).
"Workrave", retrieved from <http://www.workrave.org/>, Sep. 14, 2012. (p. 1).
"www.mydailyhealth.com" retrieved from Internet Archive Wayback Machine, 1999, 20 pages.
"Footrests—Adjustable Footrest Solutions for the Office", Ergo in Demand, Aug. 20, 2009, pp. 1-4, Ergo in Demand Inc., www.ergoindemand.com/footrest.html.
"Pulse Oximetry" SparkFun Electronics, Oct. 7, 2005 (p. 1).
"Statement in accordance with the Notice from the European Patent Office dated Oct. 1, 2007 concerning business methods" Nov. 1, 2007, 1 page, XP002456414.
Abstract for "Psychosocial job factors and symptoms from the locomotor system—a multicausal analysis", retrieved from <http://www.ncbi.nlm.nih.gov/pubmed/1962160>, May 7, 2012. (p. 1).
Abstract for "Signal Characteristics of EMG at Different Levels of Muscle Tension", retrieved from <http://onlinelibrary.wiley.com/doi/10.1111/j.1748-1716.1976.tb10195.x/abstract>, May 7, 2012. (p. 1).
Alfredo Vazquez Carazo, "Novel Piezoelectric Transducers for High Voltage Measurements", Jan. 2000, pp. 1-277.
Amato, Neil, "Top 20 companies for leadership development" CGMA Magazine, Sep. 23, 2013; available as of Dec. 13, 2015 at the website: http://www.cgma.org/magazine/news/pages/20138765.aspx?TestCookiesEnabled=redirect; pp. 1-5.
Asplund, Christopher L., et al. "A central role for the lateral prefrontal cortex in goal-directed and stimulus-driven attention." Nature neuroscience 13.4 (2010): 507-512.
Asplund, Christopher L., et al. "The attentional blink reveals the probabilistic nature of discrete conscious perception." Psychological science 25.3 (2014): 824-831.
Bed-Check Co., Bed-Check Monitoring Systems, 2006.
Berger et al. 'Investing in Healthy Human Capital'—J Occup Environ Med. (JOEM) vol. 45, No. 12, dated Dec. 2003; pp. 1213-1225.
Borah, J. "Conceptual modeling—The missing link of simulation development." Proceedings of the 2002 Spring Simulation Conference. 2002. AEgis Technologies Group; pp. 1-7.
Brown et al, "Prowess Proactive Wellness Environment Support System", Dec. 10, 2009, pp. 1-19, www.hsi.gatech.edu/onsitecenter/index.php/PROWESS.
Burkus, David, "For Leaders, Looking Healthy Matters More than Looking Smart" Harvard Business Review, Jan. 2, 2015; available as of Dec. 13, 2015 at the website: https://hbr.org/2015/01/for-leaders-looking-healthy-matters-more-than-looking-smart.
Campbell et al., "The Rise of People-Centric Sensing", IEEE Computer Society, 2008, pp. 12-21, IEEE.
Collins English Dictionary, definition of mat, 2008, retrieved at www.collinsdictionary.com.
Duke, Sean, "A 'smartphone' based defibrillator" Science Spin, Jan. 11, 2011: pp. 1-2.
Dux, Paul E., and René Marois. "The attentional blink: A review of data and theory." Attention, Perception, & Psychophysics 71.8 (2009): 1683-1700.
Dux, Paul E., et al. "Training improves multitasking performance by increasing the speed of information processing in human prefrontal cortex." Neuron 63.1 (2009): 127-138.
Electric double-layer capacitor Wikipedia; available at the website: http://en.wikipedia.org/wiki/electric_double-layer_capacitor as of Dec. 5, 2014; pp. 1-8.
Elliott, Stephen N., et al. "Cognitive load theory: Instruction-based research with applications for designing tests." Proceedings of the National Association of School Psychologists' Annual Convention, Boston, MA, February. vol. 24. 2009.
EPO: "Notice from the European Patent Office dated Oct. 1, 2007 concerning business methods" Official Journal EPO, vol. 30, No. 11, Nov. 1, 2007, pp. 592-593, XP007905525.
Fadel, Charles, et al. "Multimodal Learning Through Media: What the Research Says" Cisco Systems, Inc. (2008) pp. 1-24.
Fadjo, Cameron L., et al. "Pedagogy and Curriculum for Video Game Programming Using Scratch." Institute for Learning Technologies, Teachers College, Columbia University, New York, NY, presented at the Scratch Conference, Aug. 13, 2010; pp. 1-2.
Filmer, Hannah L., et al. "Disrupting prefrontal cortex prevents performance gains from sensory-motor training." The Journal of Neuroscience 33.47 (2013): 18654-18660.
Fougnie, Daryl, and René Marois. "What limits working memory capacity? Evidence for modality-specific sources to the simultaneous storage of visual and auditory arrays." Journal of Experimental Psychology: Learning, Memory, and Cognition 37.6 (2011): 132.

(56) References Cited

OTHER PUBLICATIONS

Georgia Tech, "Prowess Proactive Wellness Environment Support System", Dec. 12, 2009, pp. 1-27, www.hsi.gatech.edu/onsitecenter/index.php/PROWESS.

Goetzel et al. "The Relationship Between Modifiable Health Risks and Health Care Expenditures: An Analysis of the Multi-Employer HERO Health Risk and Cost Database" Journal of Occupational Environmental Medicine, vol. 40, No. 10, Oct. 1998, 30 pages.

Goetzel et al. 'Estimating the Return-on-Investment From Changes in Employee Health Risks on TheDow Chemical Company's Health Care Costs'—J Occup Environ Med. (JOEM) vol. 47, No. 8, dated Aug. 2005; pp. 759-768.

Goetzel et al. 'Health, Absence, Disability, and Presenteeism Cost Estimates of Certain Physical and MentalHealth Conditions Affecting U.S. Employers'—J Occup Environ Med. (JOEM) vol. 46, No. 4, dated Apr. 2004; pp. 398-412.

Goetzel et al. 'Second-Year Results of an Obesity Prevention Program at TheDow Chemical Company'—J Occup Environ Med. (JOEM) vol. 52, No. 3, dated Mar. 2010; pp. 291-302.

Goetzel et al. 'The Health and Productivity Cost Burden of the "Top 10" Physical and Mental HealthConditions Affecting Six Large U.S. Employers in 1999'—J Occup Environ Med. (JOEM) vol. 45, No. 1, dated Jan. 2003; pp. 5-14.

Goetzel et al. 'The Long-Term Impact of Johnson & Johnson's Health & Wellness Program onEmployee Health Risks'—J Occup Environ Med. (JOEM) vol. 44, No. 5, dated May 2002; pp. 417-424.

Goetzel et al. 'The Workforce Wellness Index'—J Occup Environ Med. (JOEM) vol. 55, No. 3, dated Mar. 2013; pp. 272-279.

Goetzel et al. The Predictive Validity of the HERO Scorecard in Determining Future Health Care Cost and Risk Trends—J Occup Environ Med. (JOEM) vol. 56, No. 2, dated Feb. 2014; pp. 136-144.

Health/Medical Writers eHealthcareWorld 2000. (May 1). MyDailyHealth.com (pp. 1-3).

Hill, Jr., Randall W.; "How Virtual Humans Can Build Better Leaders" Harvard Business Review Jul. 25, 2014; pp. 1-4.

Horseman, Samantha, et al.; "Gamefication of Health, Safety and the Environment {HSE}: An Avatarial Solution" American Society of Safety Engineers 11th Professional Development Conference & Exhibition, Bahrain, Mar. 2014;pp. 1-10.

Index for "Micro-NanoMechatronics and Human Science (MHS), 2010 International Symposium Nov. 2010", retrieved from <http://ieeexplore.ieee.org/xpl/mostRecentIssue.jsp?punumber=5658189> Ma 7, 2012. (pp. 1-5).

International Preliminary Report on Patentability for International Application No. PCT/US2012/045395, dated Jan. 7, 2014. (pp. 1-12).

International Preliminary Report on Patentability for International Application No. PCT/US2012/045401 dated Jan. 7, 2014. (pp. 1-9).

International Preliminary Report on Patentability for International Application No. PCT/US2012/045407 dated Jan. 7, 2014. (pp. 1-8).

International Preliminary Report on Patentability for International Application No. PCT/US2012/045410 dated Jan. 7, 2014, (pp. 1-8).

International Preliminary Report on Patentability for International Application No. PCT/US2012/045414 dated Jan. 7, 2014. (pp. 1-8).

International Preliminary Report on Patentability for International Application No. PCT/US2012/045419 dated Jan. 7, 2014. (pp. 1-11).

International Preliminary Report on Patentability for International Application No. PCT/US2012/045427 dated Jan. 7, 2014. (pp. 1-10).

International Preliminary Report on Patentability for International Application No. PCT/US2012/045435 dated Jan. 7, 2014. (pp. 1-10).

International Preliminary Report on Patentability for International Application No. PCT/US2012/045442 dated Jan. 7, 2014. (pp. 1-10).

International Preliminary Report on Patentability for International Application No. PCT/US2012/045447 dated Jan. 7, 2014. (pp. 1-8).

International Preliminary Report on Patentability for International Application No. PCT/US2012/045452 dated Jan. 7, 2014. (pp. 1-9).

International Search Report & Written Opinion for International Application No. PCT/US2012/045401, dated Feb. 5, 2013. (pp. 1-13).

International Search Report & Written Opinion for International Application No. PCT/US2012/045407, dated Jan. 23, 2013. (pp. 1-15).

International Search Report & Written Opinion for International Application No. PCT/US2012/045410, dated Jan. 31, 2013. (pp. 1-13).

International Search Report & Written Opinion for International Application No. PCT/US2012/045414, dated Mar. 25, 2013. (pp. 1-13).

International Search Report & Written Opinion for International Application No. PCT/US2012/045435, dated Jan. 25, 2013. (pp. 1-14).

International Search Report & Written Opinion for International Application No. PCT/US2012/045447, dated Jan. 18, 2013. (pp. 1-12).

International Search Report and Written Opinion for International Application No. PCT/US2004/045442, dated Nov. 7, 2012, pp. 1-14.

International Search Report and Written Opinion for International Application No. PCT/US2012/045395, dated Dec. 3, 2012, pp. 1-16.

International Search Report and Written Opinion for International Application No. PCT/US2012/045419, dated Dec. 6, 2012, pp. 1-16.

International Search Report and Written Opinion for International Application No. PCT/US2012/045427, dated Dec. 3, 2012, pp. 1-14.

International Search Report and Written Opinion for International Application No. PCT/US2012/045452, dated Dec. 3, 2012, pp. 1-14.

International Search Report and Written Opinion for PCT/US2014/056427 dated Apr. 22, 2015.

International Search Report and Written Opinion for PCT/US2014/069498 dated Apr. 1, 2015.

Ivanoff, Jason, Philip Branning, and René Marois. "fMRI evidence for a dual process account of the speed-accuracy tradeoff in decision-making." PLoS one 3.7 (2008): e2635. pp. 1-14.

Kelly et al. The Novartis Health Index: A Method for Valuing the Economic Impact of Risk Reduction in a Workforc—J Occup Environ Med. (JOEM) vol. 52, No. 5, dated May 2010; pp. 528-535.

Knikou, Maria. "The H-reflex as a probe: pathways and pitfalls." Journal of neuroscience methods 171.1 (2008): 1-12.

Kuriyama, Shigeru "Visualization model for a human action based on a visual perception" Measurement and Control, Japan, Journal of the Society of Instrument and Control Engineers, Dec. 10, 2006, vol. 45, No. 12, pp. 1024-1029.

\* cited by examiner

DEVICES, METHODS, AND COMPUTER MEDIUM TO PROVIDE REAL TIME 3D VISUALIZATION BIO-FEEDBACK

RELATED APPLICATIONS

This application is related to U.S. patent application Ser. No. 13/540,300 filed on Jul. 2, 2012 and titled "SYSTEMS, COMPUTER MEDIUM AND COMPUTER-IMPLEMENTED METHODS FOR MONITORING HEALTH OF EMPLOYEES USING MOBILE DEVICES", U.S. patent application Ser. No. 13/540,153 filed on Jul. 2, 2012 and titled "SYSTEMS AND METHOD TO MONITOR HEALTH OF EMPLOYEE WHEN POSITIONED IN ASSOCIATION WITH A WORKSTATION", U.S. patent application Ser. No. 13/540,028 filed on Jul. 2, 2012 and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. patent application Ser. No. 13/540,067 filed on Jul. 2, 2012 and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,095 filed on Jul. 2, 2012 and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,124 filed on Jul. 2, 2012 and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540, 180 filed on Jul. 2, 2012 and titled "SYSTEMS, COMPUTER MEDIUM AND COMPUTER-IMPLEMENTED METHODS FOR MONITORING AND IMPROVING BIOMECHANICAL HEALTH OF EMPLOYEES", U.S. patent application Ser. No. 13/540,208 filed on Jul. 2, 2012 and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", U.S. patent application Ser. No. 13/540,335 filed on Jul. 2, 2012 and titled "SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY", U.S. patent application Ser. No. 13/540,374 filed on Jul. 2, 2012 and titled "SYSTEMS, COMPUTER MEDIUM AND COMPUTER-IMPLEMENTED METHODS FOR MONITORING HEALTH AND ERGONOMIC STATUS OF DRIVERS OF VEHICLES" (now U.S. Pat. No. 8,872,640), and/or U.S. patent application Ser. No. 13/540,262 filed on Jul. 2, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", the disclosures of which are incorporated herein by reference in their entireties.

BACKGROUND OF THE INVENTION

Field of the Invention

Embodiments of the invention relate to biometrics and, more specifically, to methods, systems, and non-transitory computer-readable medium having computer program stored therein to provide three-dimensional depictions of health of human organs.

Description of the Related Art

In view of chronic health problems facing employees, employers may adopt workplace strategies to motivate and coach employees to improve their health and well-being. For example, diabetes may affect twenty percent (20%) of some populations. As will be understood by those skilled in the art, there exist a group of non-communicable diseases labeled "the big five": diabetes, cardiovascular disease, respiratory disease, cancer, and obesity. Research indicates that lifestyle is a contributing factor to the big five non-communicable diseases and may account for as much as eighty percent (80%) of the causes of these diseases.

SUMMARY OF THE INVENTION

Embodiments of the invention can include, for example, devices, methods, and non-transitory computer-readable medium having computer program stored therein to provide three-dimensional (3D) depictions of health of human organs of a user relative to the user's age based on sensed biometrics of the user.

In some embodiments, the present invention may provide a device to provide three-dimensional (3D) depictions of health of human organs of a user relative to the user's age based on sensed biometrics of the user. The device may comprise one or more processor and one or more databases in communication with the one or more processors. The databases may have a plurality of three-dimensional (3D) depictions of each of one or more human organs stored therein, the plurality of 3D depictions of each of the one or more human organs defining a set of base images of the respective human organ. Each set of base images may be configured to include a plurality of base images of the respective human organ at each of a plurality of different ages. The plurality of base images of the respective human organ at each of the plurality of different ages may be configured to include one or more depictions of the respective human organ at the respective different age at each of a plurality of health levels among a range of health levels. Each of the plurality of health levels may be configured to indicate a health risk. The device may further comprise one or more input and output units in communication with the one or more processors and positioned to receive input and output communication; one or more biometric sensors in communication with the one or more processors and configured to sense biometric parameters of a user, the user having a chronological age; one or more displays in communication with the one or more processors and configured to display an electronic user interface thereon; and a non-transitory memory medium in communication with the one or more processors, the memory medium including computer-readable instructions stored therein.

The instructions may be arranged to, when executed, cause the one or more processors to perform the operations of selecting, for each of the one or more human organs and responsive to the one or more input and output units, a first base image of the set of base images of the respective human organ that approximates a depiction of the respective human organ at the user's chronological age at a preselected one of the plurality of health levels from the one or more databases; receiving one or more biometric parameters of the user through the one or more biometric sensors to generate a plurality of biometric measurements for each of the one or more biometric parameters, each of the one or more biometric parameters associated with one of the one or more human organs; converting the plurality of biometric measurements for each of the one or more biometric parameters into electronic biometric data; determining a health-adjusted relative age of each of the one or more human organs of the user responsive to analysis of the electronic biometric data, the health-adjusted relative age configured to indicate health level of the respective human organ of the user relative to the user's age; selecting, for each of the one or more human organs, a second base image of the set of base images of the respective human organ that approximates a depiction of the respective human organ at the determined health-adjusted relative age of the respective human organ from the one or more databases; and displaying, by the electronic user interface and for a selected one or more of the one or more human organs, the first base image and the second base image thereby to enable comparison of the determined health-adjusted relative age of the respective human organ and the user's age to indicate health of the respective human organ of the user visually.

In some embodiments, the invention may provide a device to provide three-dimensional (3D) depictions of health of human organs of a user relative to the user's age based on sensed biometrics of the user. The device may include one or more processors and one or more databases in communication with the one or more processors. The databases may have a plurality of preselected three-dimensional (3D) depictions of each of one or more human organs stored therein, the plurality of 3D depictions of each of the one or more human organs defining a set of base images of the respective human organ, each set of base images configured to include a plurality of base images of the respective human organ at each of a plurality of different ages. The plurality of base images of the respective human organ at each of the plurality of different ages may be configured to include one or more depictions of the respective human organ at the respective different age at each of a plurality of health levels among a range of health levels and each of the plurality of health levels may be configured to indicate health risk. The device may further include one or more input and output units in communication with the one or more processors and positioned to receive input and output communication and a non-transitory memory medium in communication with the one or more processors.

The memory medium may include computer-readable instructions stored therein that when executed cause the one or more processors to perform the operations of selecting, for each of the one or more human organs and responsive to the one or more input and output units, a first base image of the set of base images of the respective human organ that approximates a depiction of the respective human organ at a user's age at a preselected one of the plurality of health levels from the one or more databases; sensing one or more biometric parameters of the user by use of one or more biometric sensors in communication with the one or more input and output units to generate a plurality of biometric measurements for each of the one or more biometric parameters, each of the one or more biometric parameters associated with one of the one or more human organs; converting the plurality of biometric measurements for each of the one or more biometric parameters into electronic biometric data; determining a health-adjusted relative age of each of the one or more human organs of the user responsive to analysis of the electronic biometric data, the health-adjusted relative age configured to indicate health level of the respective human organ of the user relative to the user's age; selecting, for each of the one or more human organs, a second base image of the set of base images of the respective human organ that approximates a depiction of the respective human organ at the determined health-adjusted relative age of the respective human organ from the one or more databases; and displaying, by an electronic user interface and for a selected one or more of the one or more human organs responsive to the one or more input and output units, the first base image and the second base image thereby to enable comparison of the determined health-adjusted relative age of the respective human organ and the user's age to indicate health of the respective human organ of the user visually.

Some embodiments of the present invention may provide a method to provide three-dimensional (3D) depictions of health of human organs of a user relative to the user's age based on sensed biometrics of the user. The method includes selecting, for each of one or more human organs, one of a plurality of preselected three-dimensional (3D) depictions of the respective human organ that approximates a depiction of the respective human organ at the user's age at a preselected one of the plurality of health levels. The plurality of 3D depictions of each of the one or more human organs define a set of base images of the respective human organ, each set of base images configured to include a plurality of base images of the respective human organ at each of a plurality of different ages, the plurality of base images of the respective human organ at each of the plurality of different ages configured to include one or more depictions of the respective human organ at the respective different age at each of a plurality of health levels among a range of health levels, each of the plurality of health levels configured to indicate health risk, the selected one of set of base images of the respective human organ thereby to define a first base image; sensing one or more biometric parameters of a user by use of one or more biometric sensors to generate a plurality of biometric measurements for each of the one or more biometric parameters, each of the one or more biometric parameters associated with one of the one or more human organs; converting the plurality of biometric measurements for each of the one or more biometric parameters into electronic biometric data; determining a health-adjusted relative age of each of the one or more human organs of the user responsive to analysis of the electronic biometric data, the health-adjusted relative age configured to indicate health level of the respective human organ of the user relative to the user's age; selecting, for each of the one or more human organs, a second base image of the set of base images of the respective human organ that approximates a depiction of the respective human organ at the determined health-adjusted relative age of the respective human organ; and displaying, for a selected one or more of the one or more human organs, the first base image and the second base image thereby to enable comparison of the determined health-adjusted relative age of the respective human organ and the user's age to indicate health of the respective human organ of the user visually.

Some embodiments may provide a non-transitory computer-readable medium having one or more computer programs stored therein operable by one or more processors to provide three-dimensional (3D) depictions of health of human organs of a user relative to the user's age based on sensed biometrics of the user, the one or more computer programs including a set of instructions that, when executed by the one or more processors, cause the one or more processors to perform the operations of: selecting, for each of one or more human organs, one of a plurality of preselected three-dimensional (3D) depictions of the respective human organ that approximates a depiction of the respective human organ at the user's age at a preselected one of the plurality of health levels, the plurality of 3D depictions of each of the one or more human organs thereby to define a set of base images of the respective human organ, each set of base images configured to include a plurality of base images of the respective human organ at each of a plurality of different ages, the plurality of base images of the respective human organ at each of the plurality of different ages configured to include one or more depictions of the respective human organ at the respective different age at each of a plurality of health levels among a range of health levels, each of the plurality of health levels configured to indicate health risk, the selected one of set of base images of the respective human organ thereby to define a first base image; sensing one or more biometric parameters of a user by use of one or more biometric sensors to generate a plurality of biometric measurements for each of the one or more biometric parameters, each of the one or more biometric parameters associated with one of the one or more human organs; converting the plurality of biometric measurements for each of the one or more biometric parameters into electronic biometric data; determining a health-adjusted relative age of each of the one or more human organs of the user responsive to analysis of the electronic biometric data, the health-adjusted relative age configured to indicate health level of the respective human organ of the user relative to the user's age; selecting, for each of the one or more human organs, a second base image of the set of base images of the respective human organ that approximates a depiction of the respective human organ at the determined health-adjusted relative age of the respective human organ; and displaying, for a selected one or more of the one or more human organs, the first base image and the second base image thereby to enable comparison of the determined health-adjusted relative age of the respective human organ and the user's age to indicate health of the respective human organ of the user visually.

Selecting, for each of the one or more human organs, a second base image may be responsive to the user's chronological age.

Displaying the first base image and the second base image may include displaying the first base image and the second base image in a relatively side-by-side relationship to allow for comparison between the first and second base images.

The one or more human organs may include a heart, a lung, blood vessels, a pancreas, a kidney, and a liver, wherein the one or more biometric sensors include a heart rate sensor, a peak flow respiratory rate sensor, and a blood pressure sensor. The electronic biometric data may include electronic heart data, electronic lung data, electronic blood vessel data, electronic pancreas data, electronic kidney data, and electronic liver data.

The device may further include a kiosk. At least one of the one or more displays and at least one of the one or more biometric sensors may be positioned within the kiosk.

Comparison of the determined health-adjusted relative age of the respective human organ and the user's chronological age may indicate a health risk of the user associated with the respective human organ. The one or more databases may further include a plurality of health risk profiles, each of the plurality of health risk profiles associated with one or more of the plurality of health levels.

The one or more databases may further include a plurality of biometric data of a cohort group associated with a workplace wellness program thereby to define workplace wellness data. The operations may further include: determining a health plan responsive to display of the first base image and the second base image for each of the one or more human organs; updating the workplace wellness data responsive to analysis of the determined health-adjusted relative age of each of the one or more human organs of the user; and scheduling, by the electronic user interface, a follow-up wellness appointment for the user with a lifestyle coach thereby to enhance adherence to the determined health plan.

Determining a health plan further may comprise determining a stage on the Transtheoretical model responsive to the received one or more biometric parameters. Scheduling a follow-up appointment may be responsive to the determined stage on the Transtheoretical model.

Determining a health-adjusted relative age of each of one or more human organs of the user may comprise determining a set of possible user characteristics upon which a health-adjusted relative age may be determined for the respective human organ.

Determining a health-adjusted relative age of each of the one or more human organs of the user may further comprise determining from the set of possible user characteristics for each respective human organ a set of available user characteristics responsive to signals received from the one or more biometric sensors, and processing the set of available user characteristics to determine the health-adjusted relative age of the respective human organ.

The set of base images of each respective human organ may comprise a hierarchical structure having a plurality of levels, each of the plurality of levels being associated with one or more user characteristics, the plurality of levels including at least a gender level, a height level and an age level.

It will be understood that features described in the context of one or more of the embodiments described used in combination with other embodiments. More generally, while example embodiments are described so as to provide the skilled person with an understanding of the present invention, it will be understood that the invention is not limited to the particular exemplary embodiments described.

BRIEF DESCRIPTION OF THE DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope which covers other equally effective embodiments.

DETAILED DESCRIPTION OF THE INVENTION

Figure 1:
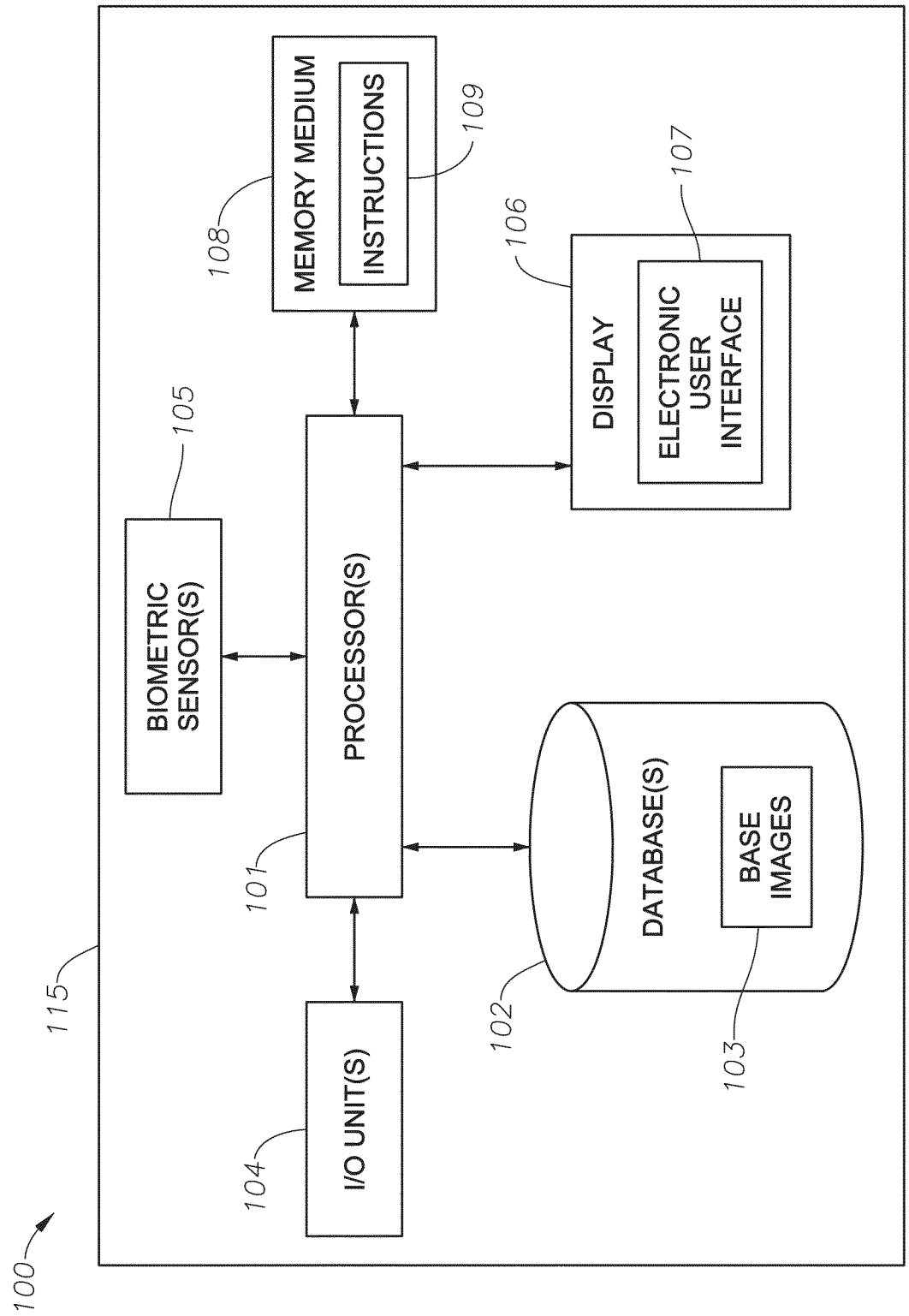
FIG. 1 is a schematic diagram of a system according to an embodiment of the invention.

So that the manner in which the features and advantages of embodiments of the invention may be understood in more detail, a more particular description of some embodiments of the invention briefly summarized above is provided with reference appended drawings, which form a part of this specification. It is to be noted, however, that the drawings illustrate only various exemplary embodiments of the present invention and are therefore not to be considered limiting, of the scope the present invention, which may include other effective embodiments.

Some embodiments, of the invention are concerned with systems and methods for determining health indicators of a user by way of biometric monitoring and for facilitating improvement in those health indicators via the provision of targeted three-dimensional (3D) visualization bio-feedback. Some embodiments of the invention comprise multiple systems that together provide a platform to provide an interactive and real-time approach to health risk appraisals (HRAs), biological age testing, lifestyle wellness coaching, 3D visualizations, and virtual reality. Embodiments provide a real-time health management system utilizing 3D visualization bio-feedback for effecting improvement in user health and well-being, and reducing both absenteeism and presenteeism.

In some embodiments, a biofeedback system can include an interactive health kiosk (or similar interactive terminal) that enables acquisition of one or more characteristics of a user. For example, an interactive health kiosk may include an interactive graphical user interface (GUI) that enables a user to submit biometric information about themselves (e.g., such as demographic information, health information, and/or the like), and/or a set of biometric sensor that can be used to acquire biometric information about the user. The kiosk may, for example, prompt the user for biometric information about themselves and/or conduct a biometric test sequence that includes employing one or more biometric sensors (e.g., a heart rate sensor, a peak flow respiratory rate sensor, a blood pressure sensor and/or the like) to collect biometric data for the user. In some embodiments, the biometric data can be used to determine a relative health status of one or more of the user's organs. For example, the biometric data may be used to determine a current heart health status, a current lung health status, a current blood vessel health status, a current pancreas health status, a current kidney health status, a current liver health status and/or the like for the user. In some embodiments, the biofeedback system can present the user with images of one or more organs that correspond to the determined health status for the respective organs. For example, if the user is determined to be 38 years of age and the user's heart is determined to be of poor health, then the health kiosk may display a 3D image that corresponds to a 38 year old heart in poor health. As described herein, if the user is 38 years old, the heat may be said to have a chronological age of 38 years, but may be said to have a health-adjusted age of 45 years based on the relatively poor health associated with the heart. In some embodiments, a health-adjusted image of an organ can be accompanied by a non-health-adjusted image of the organ to provide the user with an opportunity to compare how their organ looks relative to a "normal" organ for the user's demographic. Continuing with the above example, the kiosk may display a first 3D image that corresponds to a 45 year old heart alongside of a second 3D image that corresponds to a 38 year old heart. The depiction may be accompanied by a message that indicates that the first image corresponds to the user's heart and that the second image corresponds to a normal heart for some one that has similar demographics as the user (e.g., a person of the same gender, age, etc. as the user). It is believed that providing such a depiction may effectively communicate health conditions to users and, thereby, encourage users to take action to engage in a healthy lifestyle or maintain a healthy lifestyle. For example, if the user see a depiction of their heart that looks much worse that than a normal heart for someone of their age, the reality may encourage the user to improve their diet and engage in exercise.

FIG. 1 schematically illustrates a cybernetics information cybernetics information system 100 for providing biometric feedback by way of 3D visualizations of the health of a user's organs. The cybernetics information system 100 may include one or more processors 101 and one or more databases 102 in communication with the one or more processors 101. The one or more databases 102 may store a plurality of 3D depictions of each of one or more human organs. For example, the one or more databases 102 may store a plurality of 3D depictions of lungs, hearts, blood vessels, brains, and/or the like.

The 3D depictions of the one or more human organs may define a set of base images 103. The depictions of each of the one or more human organs may define respective sets of organ specific base images. For example, a set of 3D depictions of lungs may define a set of lung base images, a set of 3D depictions of hearts may define a set of heart base images, etc. The set of base images 103 can be configured to include a plurality of base images of each respective human organ at each of a plurality of different ages or age ranges. For example, a set of lung base images may be configured to include one or more 3D depictions of lungs corresponding to ages of 21, 22, 23, etc. and/or 20-24 years of age, 25-29, etc.

In addition, the set of base images 103 can be configured to include one or more depictions of each respective human organ at the respective different age at each of a plurality of health levels among a range of health levels. For example, a set of lung base images corresponding to a human of a particular age or age range may comprise one or more 3D depictions of a lung of a first health level (for example optimal health), one or more 3D depictions of a lung of a second health level (for example average health), one or more 3D depictions of a lung of a third health level (for example sub-optimal health), etc. Additionally, or alternatively, one or more of the respective health levels may indicate particular diseases or absence of such diseases. Further, each of the plurality of health levels can be configured to indicate one or more health risks.

The cybernetics information system 100 may also include one or more input and output (I/O) units 104 in communication with the one or more processors 101 and positioned to receive input and output communication, for example. Further, the cybernetics information system 100 can include one or more biometric sensors 105 in communication with the one or more processors 101. The one or more biometric sensors 105 can be configured to sense biometric parameters of a user. By way of example, the biometric sensors 105 may comprise one or more of a respiratory rate sensor, a blood pressure sensor, a heart rate sensor, a neural sensor, and/or the like.

The cybernetics information system 100 can further include one or more displays 106 in communication with the one or more processors 101. The one or more displays 106 can be configured to display an electronic user interface 107 thereon. Additionally, the cybernetics information system 100 can include one or more non-transitory computer readable memory medium 108 in communication with the one or more processors 101. The memory medium 108 can include computer-readable instructions 109 stored therein that when executed cause the one or more processors 101 to perform a series of operations. As is described in further detail below, the operations may include, for example, operations for determining ones of the base images 103 responsive to signals received from the one or more I/O units 104 based on user input and/or from the one or more biometric sensors 105. For example, the operations can include selecting, for each of the one or more human organs for which base images are stored in the one or more databases 102, and responsive to signals received from the one or more I/O units 104, one or more base images from a set of base images 103 of a particular human organ, at a particular age, and/or at a particular one of the plurality of health levels.

Figure 2:
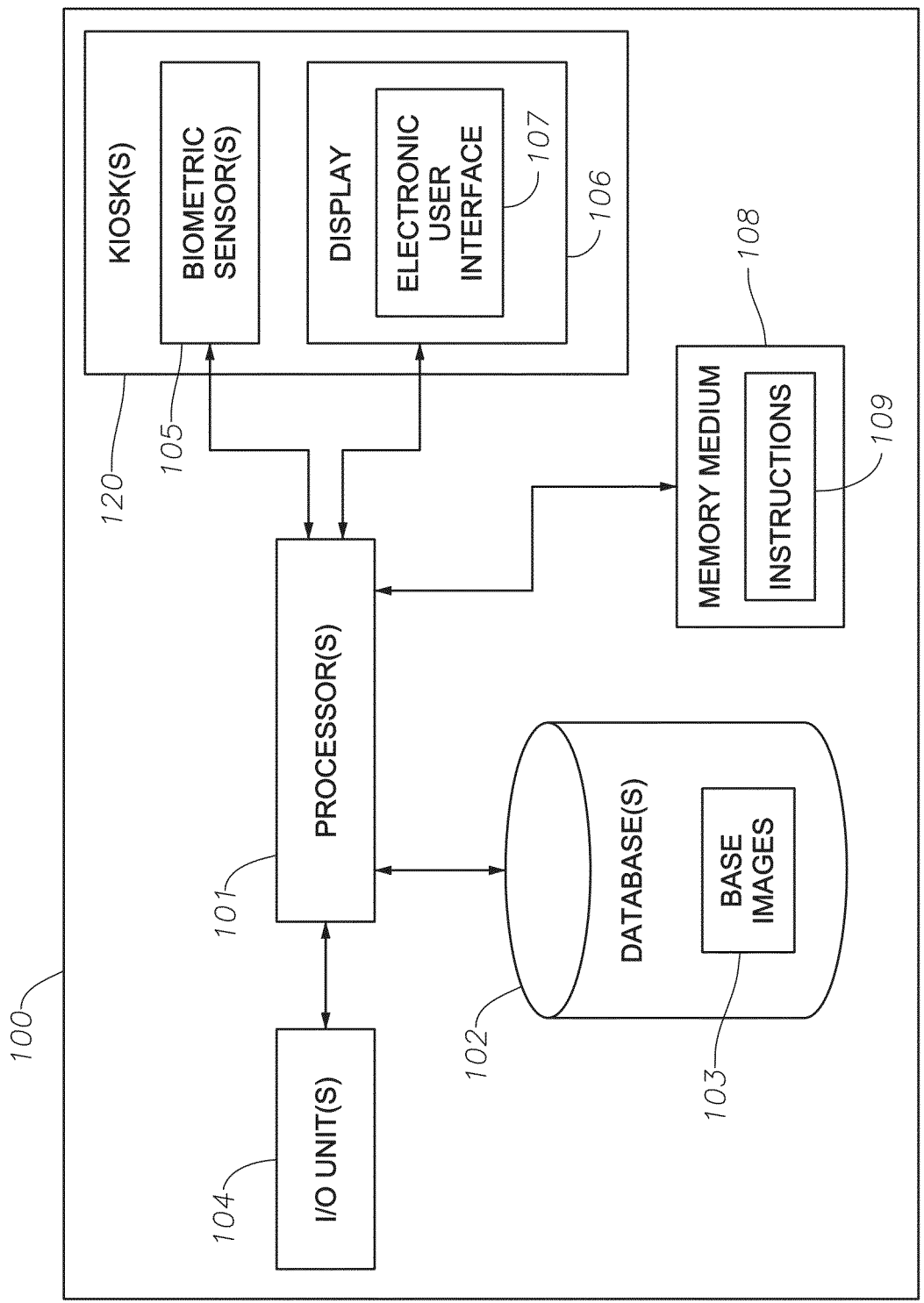
FIG. 2 is a schematic diagram of a system according to an embodiment of the invention.

In the example embodiment of FIG. 1, the cybernetics information system 100 comprises a device 115. The device 115 may be a standalone device, for example in the form of a kiosk or workstation. The device 115 may also, however, be networked to other devices to allow for communication between the device 115 and other devices (for example to receive software updates, to retrieve information from and/or store information in one or more remote databases, and/or the like). Alternatively, in some embodiments, one or more components of the cybernetics information system 100 may be provided by a plurality of devices. As schematically depicted in FIG. 2, in some embodiments, the system may comprise one or more kiosks 120. In the example embodiment of FIG. 2, a kiosk 120 comprises one or more biometric sensors 105 and one or more displays 106. In this way, the user-centric aspects of the cybernetics information system 100 (such as the displays 106 and the biometric sensors 105) may be conveniently located within and throughout a user's environment, such as a workplace or community.

In the example embodiment of FIG. 2, the one or more processors 101, the one or more databases 102, the one or more I/O units 104 and the one or more memory medium 108 are not housed within the kiosk 120. The one or more processors 101, the one or more databases 102, the one or more I/O units 104 and the memory medium 108 may be housed within one or more separate devices (not depicted).

Figure 3:
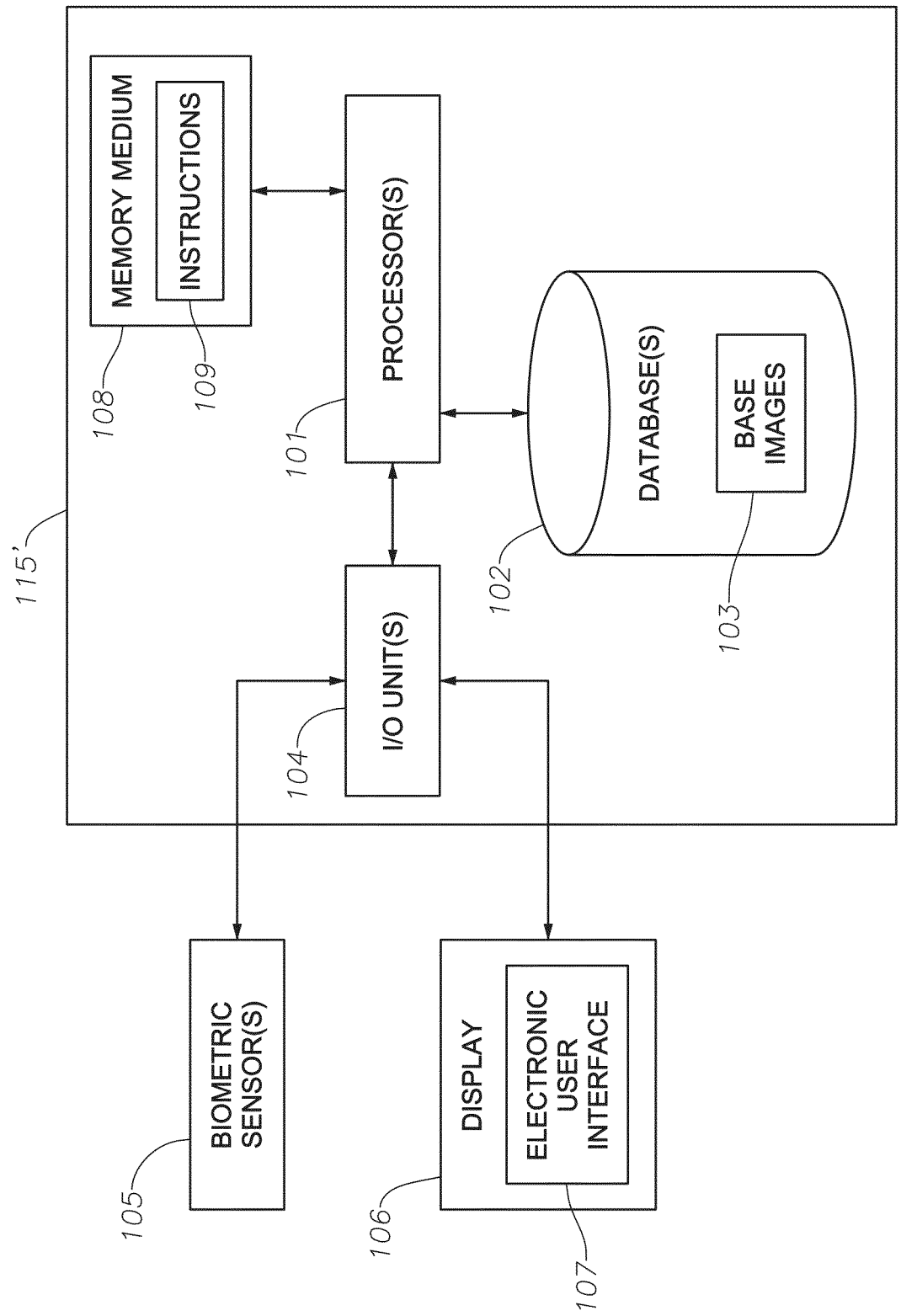
FIG. 3 is a schematic diagram of a system according to an embodiment of the invention.

FIG. 3 schematically illustrates a further example arrangement of the cybernetics information system 100. In the example embodiment of FIG. 3, the display 106 and the biometric sensors 105 are external and distinct from a device 115', but are not provided within a kiosk. For example, either or both of the biometric sensors 105 and/or the display 106 may be provided by one or more of a user's own devices. For example, in some embodiments, the cybernetics information system 100 may allow for a user to connect her own devices to the one or more I/O units 104 provided by the device 115', for interfacing with the one or more processors 101 and thereby providing three-dimensional (3D) depictions of health of a user's organs on the display 106. In this way, for example, a user may utilize sensors and/or displays provided by a mobile device (such as a smartphone), sensors provided within a personal activity tracker, and/or the like.

In light of the foregoing, it will be appreciated that while preferred and advantageous embodiments are depicted in FIGS. 1-3, the components of the cybernetics information system 100 may be arranged differently in other embodiments. For example, with reference to the example embodiment of FIG. 3, in some embodiments, one or more biometric sensors 105 may be provided by the device 115' with only the display 106 being provided separately. Similarly, in other embodiments, the display 106 may be provided by the device 115' with only the biometric sensors 105 being provide desperately. In any event, it is to be understood that the cybernetics information system 100 may be arranged in any appropriate manner as will now be apparent to the skilled person. It will be further be appreciated that each of the connections between each of the components of the cybernetics information system 100 may be implemented in any appropriate manner, using any combination of, for example, wired and/or wireless connections.

Figure 4:
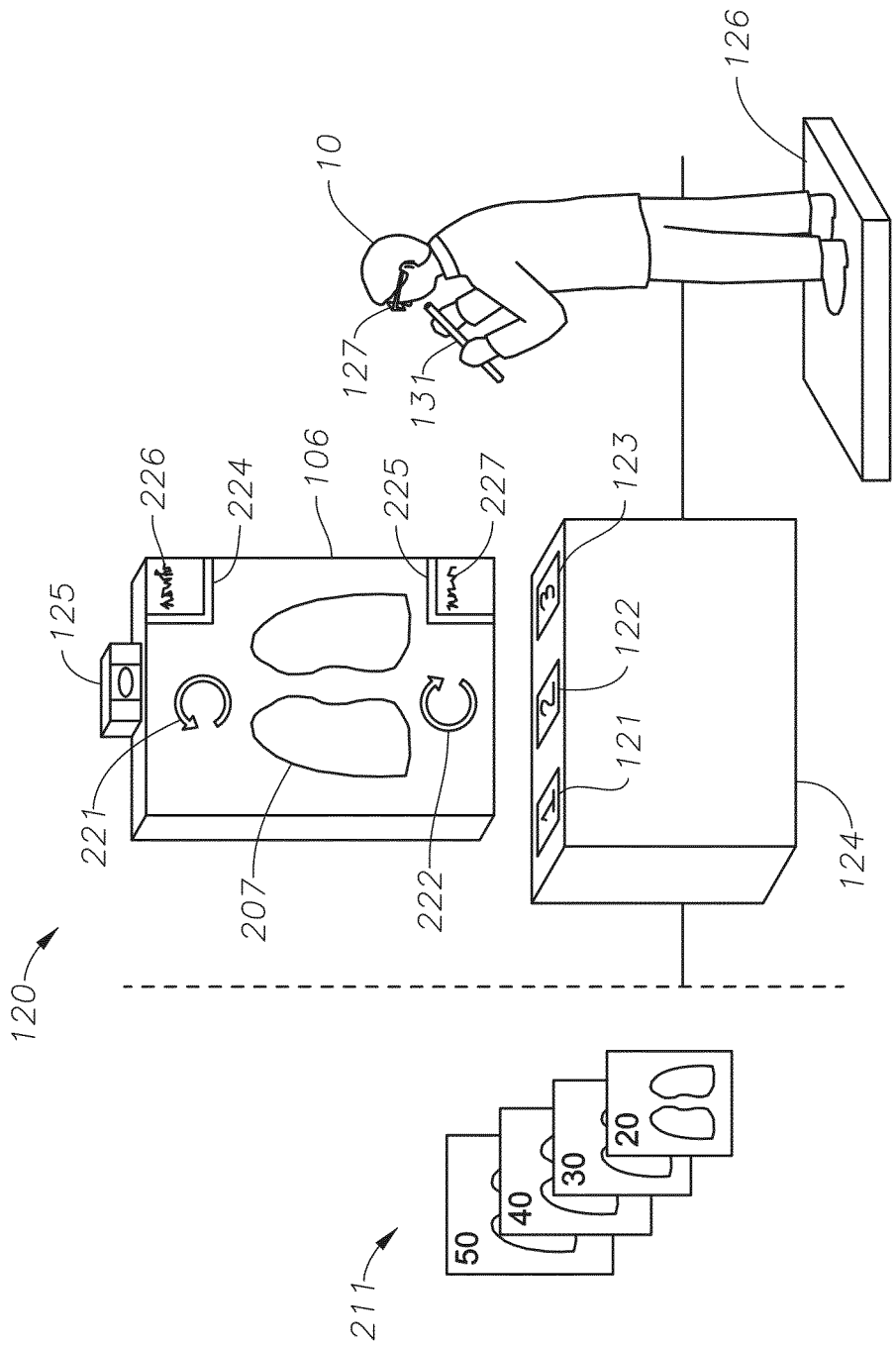
FIG. 4 is a schematic diagram of a system including a kiosk operating a lung health module according to an embodiment of the invention.
Figure 8:
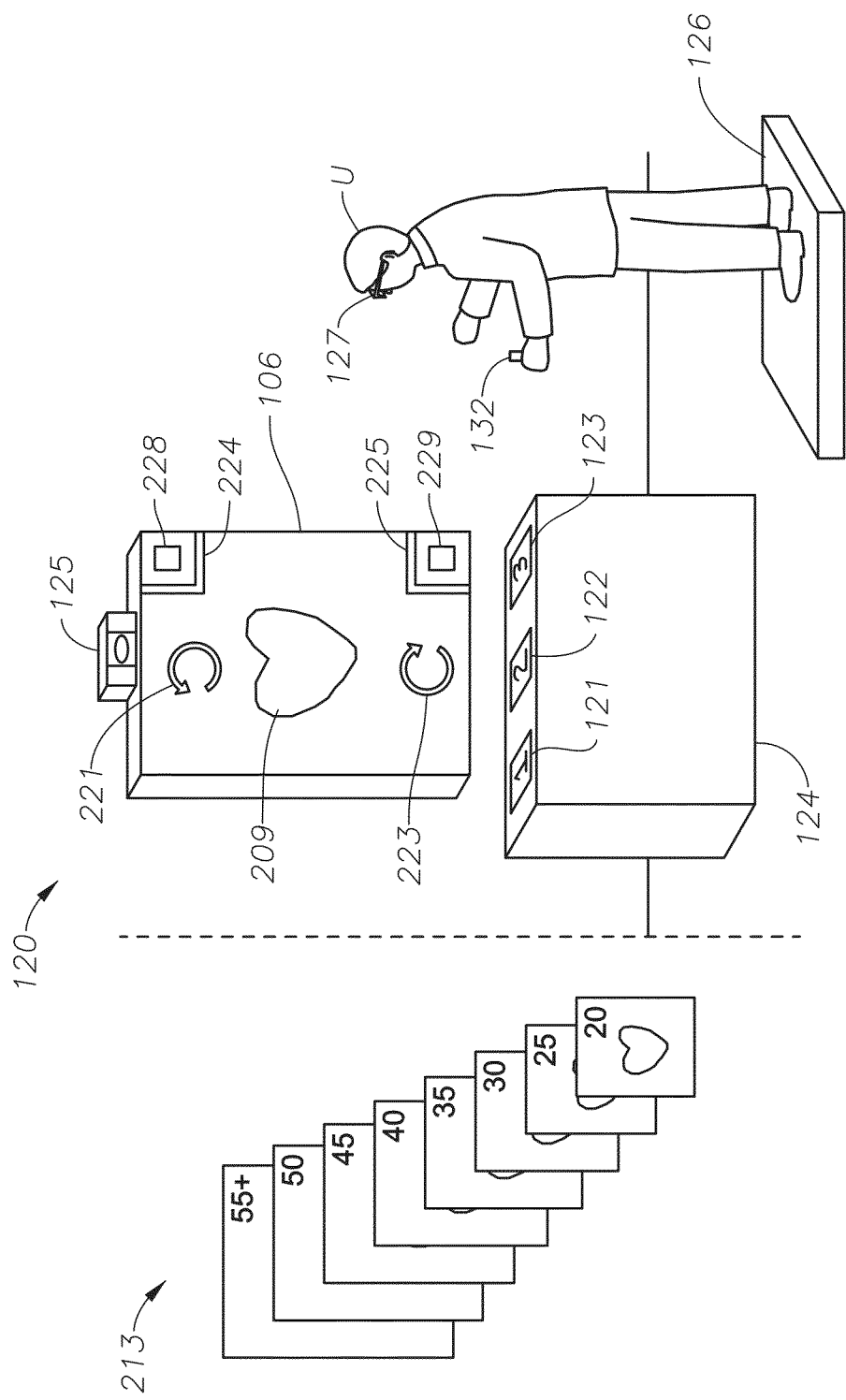
FIG. 8 is a schematic diagram of a system including a kiosk operating a heart health module according to an embodiment of the invention.
Figure 9:
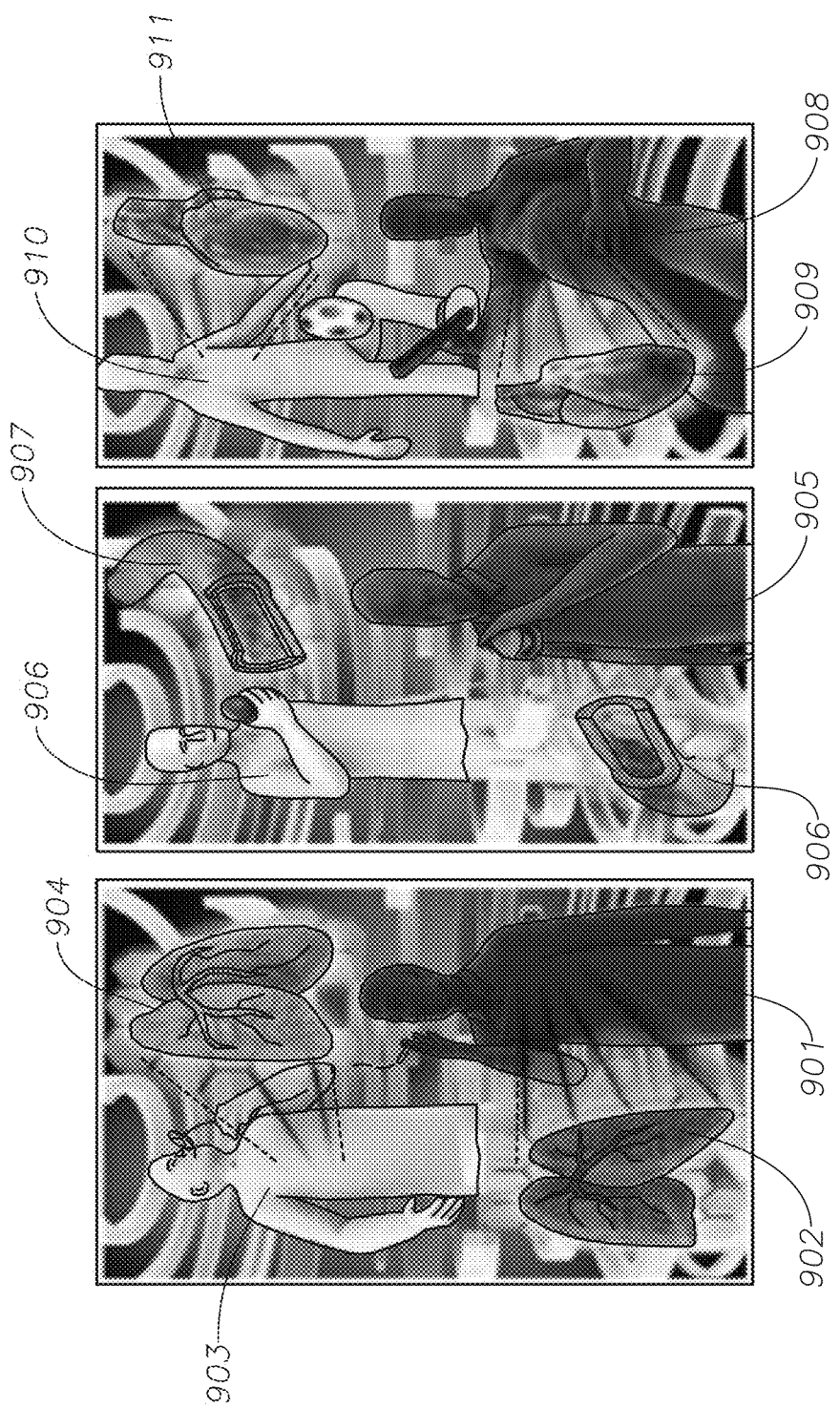
FIG. 9 is an illustration of visualizations that may be provided in accordance with an embodiment of the invention.

FIGS. 4, 8, and 9 further illustrate the present invention according to exemplary embodiments and depict a kiosk 120 in use by a user 10. The kiosk 120 comprises a base portion 124 and a display 106. The base portion 124 may, in some embodiments, house components of the cybernetics information system 100 such as the one or more processors 101, the one or more databases 102, the one or more I/O units 104, and/or any other components. In the example of FIG. 4, the base portion 124 further comprises three buttons 121, 122, 123 for allowing the user 10 to interact with the electronic user interface 107. It will be appreciated, however, that any number of buttons or other input devices may be provided. The kiosk 120 further comprises a camera 125 positioned above the display 106. It will be appreciated, however, that where provided, the camera 125 may be positioned in any appropriate location. The camera 125 may form a part of the one or more biometric sensors 105.

The user 10 stands on a platform 126 which is arranged to position the user 10 in front of the kiosk 120 facing the display 106. The platform 126 may comprise markings to indicate an optimal standing position for the user 10. The platform 126 may comprise one or more of the biometric sensors 105. For example, the platform 126 may provide a weight sensor (not shown) for sensing a weight of the user 10. As a further example, the platform 126 may comprise a bioelectric impedance sensors (not shown) arranged to determine a body composition of the user 10 by applying an electrical current to the feet of the user 10.

The user 10 may interact with the electronic user interface 107 to initialize a 3D visualization bio-feedback system. For example, the user may interact with the electronic user interface 107 to identify herself to the cybernetics information system 100 (for example through a log-in process). Identification of the user 10 may be effected by way of the user 10 entering information manually, using the buttons 121, 122, 123, for example. Information may alternatively be entered using any other means such as through gesture recognition, where gestures may be captured by the camera 125 and processed by the one or more processors 101 to determine corresponding input operations. In some embodiments, identification may be automatic. For example, in some embodiments a facial recognition system such as the SHORE™ system from Fraunhofer IIS may be used to detect faces in images captured by the camera 125.

To aid accuracy of identification, facial recognition may be combined with other biometric measurements, such as, for example, a weight measurement obtained through a weight sensor disposed within the platform 126. As will be described in more detail below, where the user 10 identifies herself to the cybernetics information system 100, information captured by the system 10 (for example by the biometric sensors 105 and inputs received from the user 10) may be stored in one or more health records associated with the user 10. Additionally or alternatively, health records containing information previously stored about the user 10 may be retrieved. For example, a chronological age of the user 10 may be retrieved, together with any health goals and health plans, as is discussed in more detail below. In some embodiments, identification of the user 10 may not be necessary to use the cybernetics information system 100. For example, in some embodiments, the cybernetics information system 100 may allow a user to use the system as an unidentified, or "guest" user. In embodiments in which a user 10 need not be personally identified, the user 10 may nonetheless interact with the electronic user interface 107, in order to provide information, such as chronological age.

The cybernetics information system 100 may provide for 3D visualization bio-feedback responsive to a plurality of biometric inputs. For example, the computer readable instructions 109 may comprise one or more modules for providing 3D visualization bio-feedback for each of a plurality of respective human organs. By way of further example, the instructions 109 may comprise, a lung 3D visualization bio-feedback module, a blood vessel 3D visualization bio-feedback module and/or a heart 3D visualization bio-feedback module. It will be appreciated that the cybernetics information system 100 may provide for 3D visualization bio-feedback of different and/or additional organs than those described herein. The user 10 may therefore also interact with the electronic user interface 107 to select one or more of the provided 3D visualization bio-feedback modules.

Referring particularly to FIG. 4, the depicted kiosk 120 is arranged to provide a lung 3D visualization bio-feedback module. The kiosk 120 is arranged to monitor biometric characteristics of the user 10 so as to obtain electronic lung data. In particular, in the example embodiment of FIG. 4, the electronic lung data comprises electronic peak respiratory flow rate (PEFR) data. The user uses a peak respiratory flow rate (PEFR) meter 131 which is configured to measure a maximum speed of expiration and to convert the measured speed into electronic PEFR data. The electronic PEFR data is provided to the cybernetics information system 100 (for example to the one or more processors 101 through the I/O units 104). Responsive to receiving the electronic PEFR data from the PEFR meter 131, the cybernetics information system 100 is arranged to provide 3D visualization bio-feedback images for presentation on the display 106. In particular, for a lung 3D visualization bio-feedback module as depicted in FIG. 4, the cybernetics information system 100 is arranged to display one or more 3D images 207 of a lung on the display 106.

Figure 5:
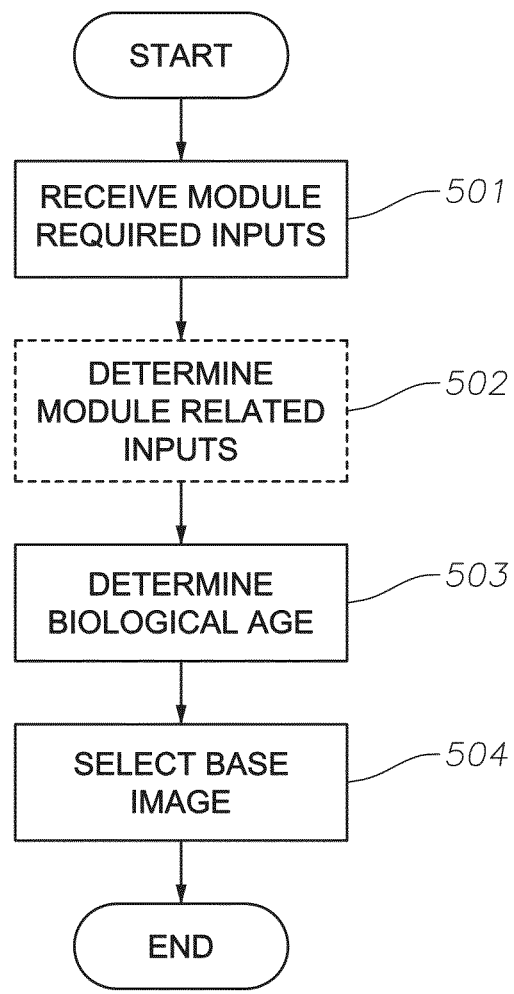
FIG. 5 is a flowchart illustrating processing that may be carried out to provide 3D visualization bio-feedback according to an embodiment of the invention.

FIG. 5 is a flowchart illustrating processing that may be carried out by the cybernetics information system 100 in some embodiments to generate the one or more 3D images for presentation on the display 106. At a step 501, module required inputs are received. Module required inputs may be inputs which the module needs to receive in order to be able to generate the one or more 3D images for presentation on the display 106. For example, module required inputs for a lung module may comprise electronic lung data. The electronic lung data may comprise the electronic PEFR data from the PEFR meter 131. It will be appreciated that other module required inputs may be defined and received at step 501.

In some embodiments, following receipt of the module required inputs at step 501, one or more module related inputs may be determined at step 502. Determination of module related inputs may comprise a determination of a set of possible characteristics. The set of possible characteristics may comprise one or more characteristics which may be related to a particular module and/or organ. For example, for a lung module, a set of possible characteristics may comprise characteristics such as gender and height. The set of possible characteristics may be determined, at least in part, by information stored in a module data store. For example, a lung module data store may store may comprise records correlating electronic PEFR values with one or more characteristics. For example, in some embodiments, a lung module data store may store records correlating PEFR values (or average PEFR value ranges, for example) with each of a plurality of ages, or age ranges. The PEFR values (or average PEFR value ranges) may be, for example, average PEFR values for that age, or ideal PEFR values for that age. In some embodiments, a lung data store may store records correlating electronic PEFR values with one or more other characteristics such as weight, height, gender, etc. As such, the method at step 502 may comprise determining what, if any, characteristics are stored by, and may be queried in, a module data store. A module data store may be stored in the one or more databases 102, or may be stored remotely from the kiosk 120 and made available for querying via one or more network connections.

Determining a set of module related inputs at step 502 may comprise processing signals received from the biometric sensors 105 to determine one or more available characteristics. For example, if it is determined that the set of possible characteristics comprises age, height and gender, determining module related inputs at step 502 may comprise processing signals received from the camera 125 (and/or other sensors) in order to automatically determine the age, height and gender of the user 10. Similarly, if it is determined that the set of possible characteristic comprises weight, determining module related inputs at step 502 may comprise processing signals received from a weight sensor within the platform 126 to automatically determine the weight of the user 10. In some embodiments, where automatic determination of one or more of the possible characteristics is unsuccessful (for example the face of the user 10 is obstructed from the camera 125) a prompt may be provided (for example visually, audibly, etc.) to direct the user 10 to remove any obstruction to the automatic determination, or to manually enter the relevant information. Where only some of the set of possible characteristics are available to the cybernetics information system 100 (for example because one or more characteristics cannot be determined automatically and the user 10 has not provided this information manually), further processing, in some embodiments, may be based only on the available characteristics.

At step 503, the module required inputs and any module related inputs may be processed to determine an organ specific health-adjusted relative age (also known as an organ specific biological age). Determining an organ specific health-adjusted relative age for the user 10 may comprise interrogating a module data store to determine an age, or age range, associated with the received electronic biometric data and any other available characteristics. That is, as described above, a module data store may provide records associating one or more biometric characteristics with a particular age or age range, among other characteristics. In this way, by interrogating the module data store based on the inputs received from the user 10 at steps 501, 502, the cybernetics information system 100 can determine a health-adjusted relative age associated with the inputs from the user 10. It will be appreciated that the health-adjusted relative age determined based on the inputs received at steps 501, 502 may not match the chronological age of the user 10.

By way of example, with reference to FIG. 4, upon receiving electronic PEFR data from the PEFR meter 131 at step 501, and determining any lung module related inputs at step 502, the cybernetics information system 100 may be arranged to determine a health-adjusted relative lung age for the lungs of the user 10. Determining a health-adjusted relative lung age of the user 10 may comprise interrogating a lung module data store to determine an age, or age range, associated with the received electronic PEFR data.

After determining an organ specific health-adjusted relative age at step 503, an image may be selected from a subset of lung base images 211 (FIG. 4) responsive to the determined organ specific health-adjusted relative age and responsive to any one or more of the inputs received. It will be appreciated that the set of base images 103 may be associated with ones of the possible characteristics in any convenient manner, and that processing at step 503 to select a particular one of the base images 103 may vary in accordance with the particular associations with ones of the particular characteristics. In FIG. 4, for example, each of the images 211 is associated with an age range (i.e. 20-24, 25-29, 30-34, 35-39, 40-44, 45-49, 50-54 and 55+).

Figure 6A:
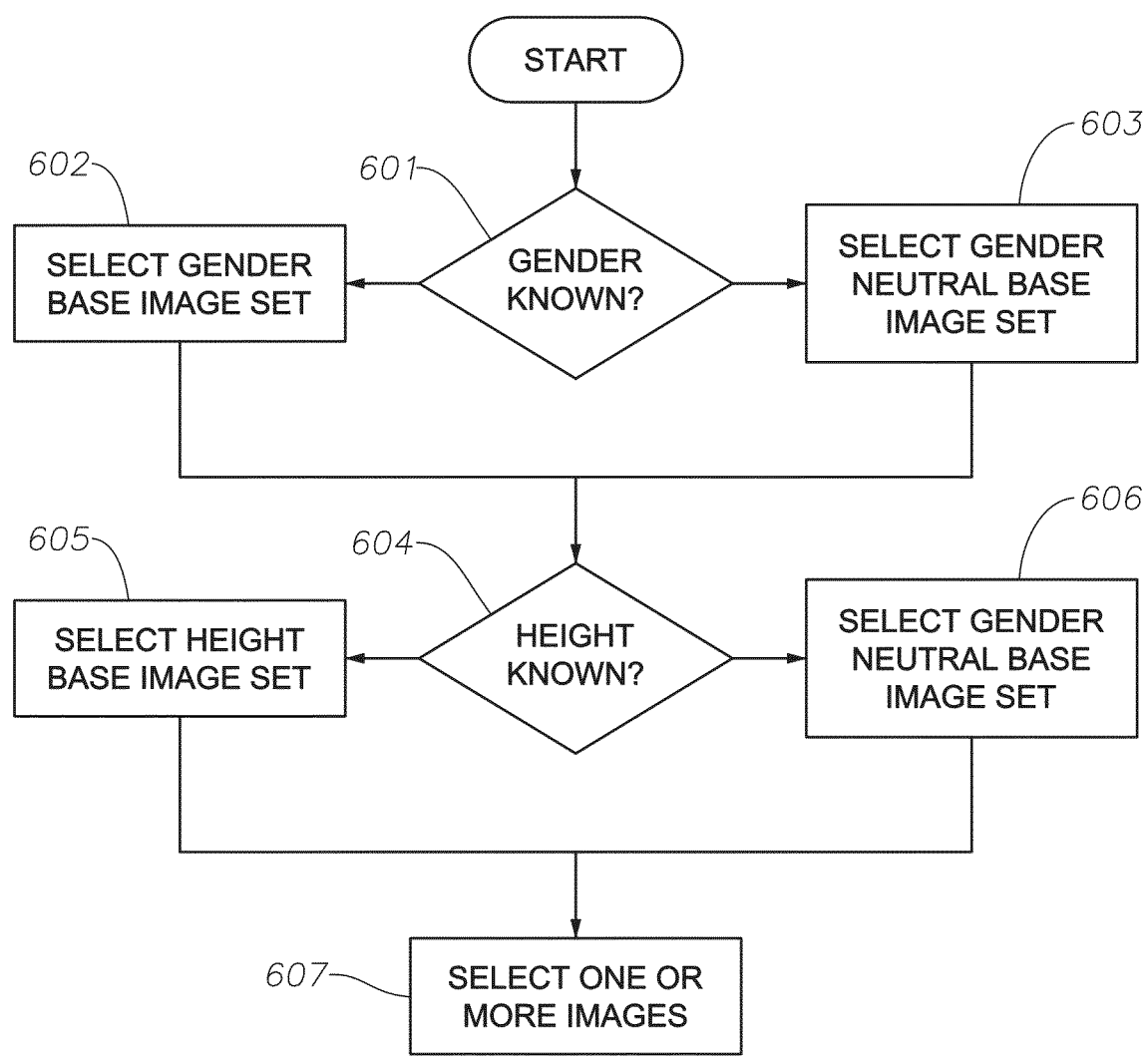
FIG. 6A is a flowchart illustrating processing that may be carried out to determine 3D image according to an embodiment of the invention.
Figure 6B:
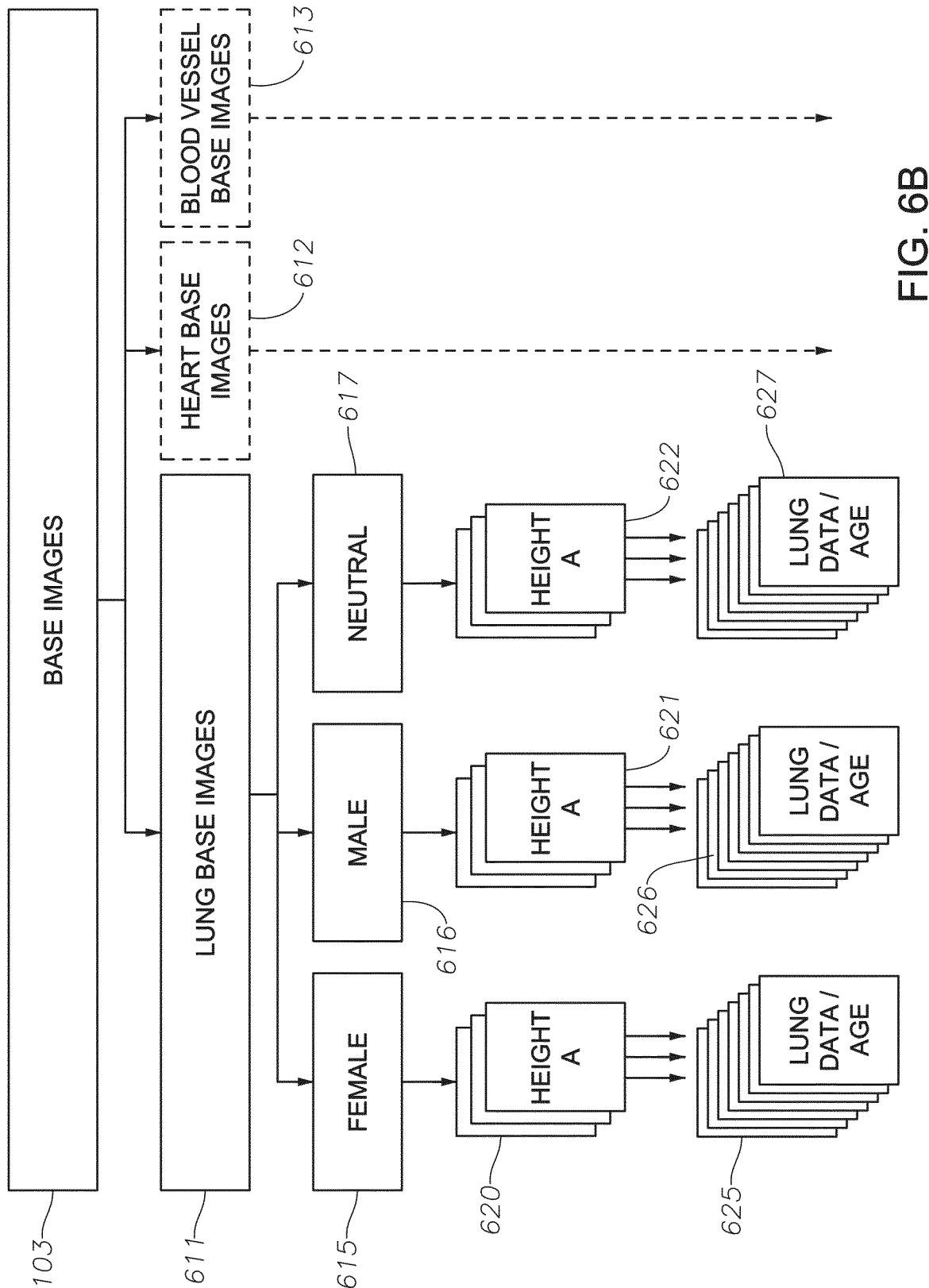
FIG. 6B is a schematic diagram of a structure of 3D representations of organs according to an embodiment of the invention.

FIG. 6A is a flowchart showing an exemplary method of selecting a lung image from the set of base images 103, which may be used in accordance with some embodiments of the invention. FIG. 6B schematically illustrates an exemplary structure of the set base images 103 in accordance with some embodiments. In FIG. 6B, the set of base images 103 comprises a subset of lung base images 611, a subset of heart base images 612 and a subset of blood vessel base images 613. For clarity, only the structure of the subset of lung base images 611 is depicted in further detail in FIG. 6B, although it will be understood that in some embodiments, other subsets of base images may be structured similarly to the subset of lung base images 611. While the method and structure illustrated in FIGS. 6A, 6B advantageously allows for the efficient determination of one or more of the base images, it is to be understood that other methods may be used.

Referring to FIG. 6A, at step 601 it is determined whether a gender of the user 10 is known. As described above, a gender of the user 10 may be available from an automatic gender determination based, for example, upon processing of image data received from the camera 125, or may have been manually provided by the user 10. If it is determined at step 601 that the gender of the user 10 is known, the method may proceed to step 602 where a gender-specific base image subset from the subset of lung base images 611 may be selected. For example, if the user 10 is female, a female-specific subset of base images 615 (FIG. 6B) may be selected from a subset of lung base images 611, while if the user 10 is male, a male-specific subset of base images 616 may be selected from the subset of lung base images 611. If, on the other hand, it is determined at step 601 that the gender of the user 10 is not known, the method may proceed to step 603 where a gender-neutral subset of base images 616 may be selected. It will be appreciated that in other embodiments, were a gender of the user is not known and a gender neutral subset is not available, one of the subsets 615, 616 may be selected at step 603.

At step 604 it may be determined whether the height of the user is known. If it is determined that the height of the user is known, the method may proceed to step 605 at which one of a height-specific base image subset may be selected from the gender-specific (or neutral) subset selected earlier. For example, with reference to FIG. 6B, the female-specific base image subset 615 comprises a plurality of height-specific subsets 620, the male-specific base image subset 616 comprises a plurality of height-specific subsets 621 and the gender-neutral base image subset 617 comprises a plurality of height-specific subsets 622.

On the other hand, if it is determined at step 604 that the height of the user 10 is not known, the method may proceed to step 606 at which a height-neutral subset may be selected. For example, each of the subsets 620, 621, 622 may comprise a height-neutral (or "default") subset to be selected in the event that the height of the user 10 is not known. From each of steps 605 and 606, the method proceeds to step 607 at which the received electronic lung data is used to select one or more lung images. For example, each of the subsets 620, 621, 622 may have respective subsets of lung images 625, 626, 627. Each image in the subsets 625, 626, 627 may be associated with both a lung characteristic (for example PEFR value) and an age. At step 607, therefore, the method may select a first image from one of the subsets 625, 626, 627 based on a user's chronological age (if known), and select a second image from one of the subsets 625, 626, 627 based on the received electronic lung data (for example received electronic PEFR data). The first image may indicate, for example, an average (or ideal) lung given the details known about the user 10 (for example height, gender, age, etc.) while the second image may to the health-adjusted relative age of the lungs of the user. Indeed, it will be appreciated that in some embodiments, the second image may be selected based upon the calculated health-adjusted relative age determined in processing such as that shown in FIG. 5. By selecting two images, a first representing a healthy organ and a second representing the user's actual organ, the cybernetics information system 100 provides the user 10 with a tool to compare the health of their organs with healthy organs.

In some embodiments, the base images 103 may be structured to further assist in identification of appropriate ones of the base images and to provide additional information to the user 10. For example, in some embodiments, the base images 103 may further be structured to allow identification of health issues, such as diseases, and risk factors. For example, while in the above described example, a user's chronological age was used to select a first image (for example indicative of a healthy organ), in some embodiments, a user's chronological age may also be processed to select the second image (for example indicative of the user's actual organ). In some embodiments, therefore, while a user with a chronological age of, say, 25, may be determined to have a health-adjusted relative lung age of, say, 40, the second image selected (to represent the user's health-adjusted relative lung age) may be different to the image that would be selected for a healthy user with both a chronological age and health-adjusted relative lung age of 40. In some embodiments, the second image selected may depict one or more diseases or problems which may be determined from the disparity between the chronological age and the health-adjusted relative age of the user 10 together with any other known information (for example history of smoking, dietary issues, etc.).

As shown in FIG. 4, the selected image(s) are displayed on the display 106 as images 207. The selected image may be displayed in three dimensions (3D). For example, the user 10 may wear 3D glasses 127. Alternatively, the display 106 may be an autostereoscopic display, a holographic display or any other form of display to allow images to be viewed in 3D. In some embodiments, the display 106 may comprise a virtual reality headset to allow the user 10 to view the selected image in 3D. There may also be displayed manipulation objects, such as rotation arrows 221, 222. The user 10 may interact with the manipulation objects to manipulate the images 207, for example through rotation, translation and scaling. Additional information may be displayed to the user 10. For example, one or more information boxes 226, 227 may provide instructions, prompts, indications of readings obtained from the biometric sensors 105, and/or the like. Additionally, information may be displayed to convey to the user the health-adjusted age determined at step 503.

Figure 7:
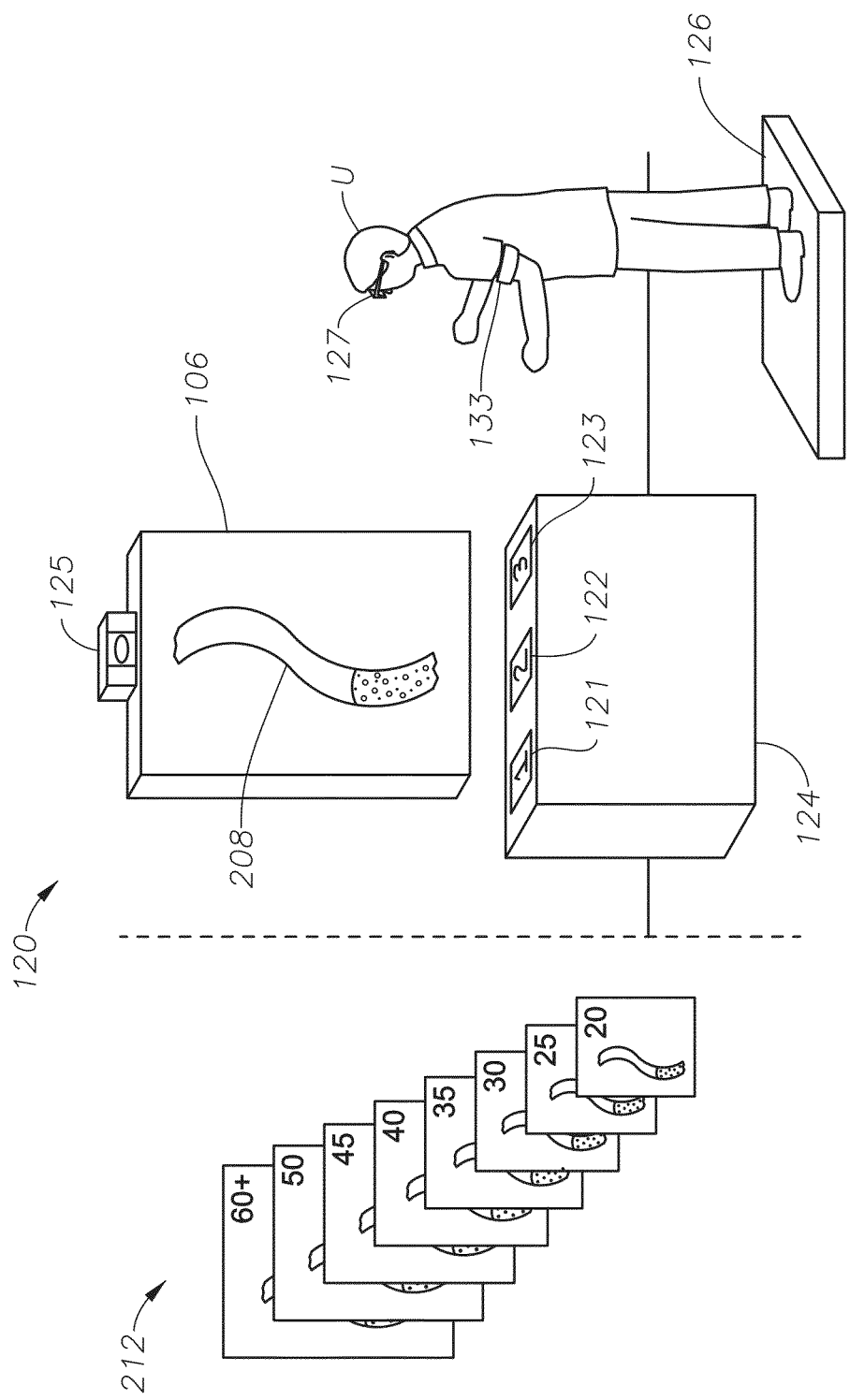
FIG. 7 is a schematic diagram of a system including a kiosk operating a vascular health module according to an embodiment of the invention.

FIGS. 7 and 8 depict the kiosk 120 arranged to provide a heart 3D visualization bio-feedback module and a blood vessel 3D visualization bio-feedback module respectively. Referring to FIG. 7, the biometric sensors 105 may further comprise a blood pressure sensor 133. In the depicted example, the blood pressure sensor 133 takes the form of a blood pressure cuff, although it will be appreciated that any blood pressure sensor may be used. In a similar manner to that discussed above in connection with the lung 3D visualization bio-feedback module, the cybernetics information system 100 may utilize measurements from the blood pressure sensor 133, in combination with any other information, in order to determine, by way of the method of FIG. 5 or similar, a health-adjusted relative blood vessel age for the blood vessels of the user 10 by querying an blood vessel module data store. The cybernetics information system 100 may then use the health-adjusted relative blood vessel age to select one or more base images 212 to display to the user 10, by way of the method of FIG. 6A or similar. For example, in some embodiments, the cybernetics information system 100 may use one or more obtained characteristics of the user 10 to select a set of images 212 from the set of base images 103 and use the health-adjusted relative blood vessel age to select one or more of the images 212. The cybernetics information system 100 may then display the selected one or more of the images 212 to the user 10.

Referring to FIG. 8, the biometric sensors 105 may comprise a heart rate sensor 132. In FIG. 8, the heart rate sensor 132 is a hand-held heart rate sensor, but it will be appreciated that the heart rate sensor 132 may take any form. The cybernetics information system 100 may utilize measurements from the heart rate sensor 132, in combination with any other available information, to determine a health-adjusted relative age of the heart of the user 10 by querying a heart data store. The cybernetics information system 100 may then use the health-adjusted relative heart age to select a set of images 213 from the set of base images 103 and use the health-adjusted relative heart age to select one or more of the images 213. The cybernetics information system 100 may then display the selected on or more of the images 213 to the user 10.

As indicated above, in some embodiments, in addition to displaying a representation of the organs of the user 10, the cybernetics information system 100 may display one or more additional representations of organs. In some embodiments, for example, if the health-adjusted relative age of a user's organ indicate poor organ health (for example the health-adjusted relative age of the user's organs is greater than the user's chronological age), the cybernetics information system 100 may additionally display a chronological age dependent 3D depiction of a corresponding healthy organ. The chronological age dependent 3D depiction of healthy organs may additionally be responsive to any other available characteristics of the user 10 such as gender, height, etc. as discussed above. Providing a 3D depiction of a healthy organ provides the user 10 with concrete and experiential learning feedback, which provides a powerful psychological impetus to effect behavior modifications. In some embodiments, a further depiction of an unhealthy organ may be displayed where a user's organ is deemed to be healthy, in order to provide motivation to maintain organ health.

FIG. 9 illustrates an example of a 3D visualization bio-feedback that may be provided on the display 106 in some embodiments of the invention. A first panel of FIG. 9 illustrates a display that may be provided as part of a lung 3D visualization bio-feedback module. In a lower portion of the first panel, a depiction 901 of the user 10 is presented, together with a depiction 902 of the user's lungs. In the example of FIG. 9, the user 10 is in relatively poor health and is depicted smoking. For comparison and motivation, a depiction 903 of the user 10 in a healthy state is depicted in an upper portion of the first panel, together with a depiction 904 of healthy lungs for a person of the same chronological age as the user 10.

A second panel of FIG. 9 illustrates a display that may be provided as part of an blood vessel 3D visualization bio-feedback module. In the second panel of FIG. 9, a depiction 905 of the user 10 eating unhealthy food is displayed, together with a depiction 906 of the blood vessels of the user 10. In an upper portion of the second panel of FIG. 9, a depiction 906 of the user eating healthy food is displayed, together with a depiction 907 of healthy blood vessels for someone of the user's age. A third panel of FIG. 9 illustrates a display that may be provided as part of a heart 3D visualization bio-feedback module. In the third panel of FIG. 9, a depiction 908 of the user in a sedentary state (watching television) is displayed together with a depiction 909 of the heart of the user 10. In an upper portion of the third panel of FIG. 9, a depiction 910 of the user in an active state (kicking a ball) is displayed together with a depiction 911 of a healthy heart for a person of the same age as the user 10.

The database 102 may comprise a plurality of health risk profiles. Each of the plurality of health risk profiles may be associated with one or more of a plurality of health levels. A health risk profile may therefore be selected responsive to selection of one of the base images, and/or responsive to determination of a health-adjusted relative organ age. The health risk profile may indicate health risks and may be used within a wellness program (such as a workplace wellness program). For example, as described below with reference to FIG. 16, the cybernetics information system 100 may be integrated within a networked arrangement of devices configured to provide a wellness program. As described above, the database 102 (or an external database) may provide one or more records for the user 10 (and more generally for a cohort of the wellness program). Determination of a health-adjusted relative age, selection of a health risk profile and/or determination of one or more health levels, may be used to update information stored for the user 10 within the wellness program, and as is described below with reference to FIG. 15, may be used to schedule further wellness interventions.

A plurality of biometric sensors 105 have been described above. It will be appreciated, however, that the biometric sensors 105 may comprise any number or combination of biometric sensors, including, for example, blood condition sensors (such as blood glucose sensors, blood oxygen sensors, blood cholesterol sensors, etc.), neural sensors (such as EEG sensors configured to measure neural activity—for example alpha, beta, delta, gamma, theta, etc. brain waves), strength sensors, body composition sensors (for example, bioelectrical impedance sensors, ultrasound, x-rays, millimeter wave scanners, etc.), substance sensors (such as sensors for detecting nicotine product use, and blood alcohol content sensors such as "breathalyzers"). One or more computer programs may be executed on the one or more processors 101 to process received biometric data from the biometric sensors 105. For example, where one or more neural sensors are provided, software such as BioGraph Infiniti® from Thought Technology Ltd, and/or BrainMaster Discovery® from BrainMaster Technologies, Inc., and/or the like, may be used to process received neural data.

In some embodiments, the cybernetics information system 100 may be used to provide an automated Health Risk Appraisal and/or for providing the user 10 with a health goals and/or a health plan. Many organizations rely on self-reported questionnaires as a method for conducting HRAs of its members. Research has shown that demonstrated that organizational interventions which monitor health risk indicators (for example body mass index (BMI), blood pressure (BP), body fat percentage, physical activity levels, stress, smoking, lower back pain, etc.) and facilitate and encourage reductions in risk factors, can reduce an organizations costs, generate physiological improvements, improve job satisfaction among employees, help employees manage stress more effectively, improve employee work engagement and productivity. Generally, current methods to measure health risks and health status of individuals is through the application of a self-assessment Health Risk Appraisal (HRA).

An HRA may identify common modifiable risk factors related to non-communicable diseases (for example, the "Big Five" non-communicable diseases as identified by the World Health Organization—cancer, cardiovascular diseases, diabetes, respiratory disease and obesity). HRAs generally take the form of a questionnaire and analyze specific health behaviors and lifestyle characteristics, such as: nutrition, physical activity, blood glucose levels, smoking habits, resting heart rate, cholesterol levels, weight, blood pressure, etc. An HRA may utilize a demographic profile of health risks and lifestyle habits of a given population to assist individuals to better understand their health risks and may be used to facilitate the provision of advice for further actions to be taken by that individual to improve wellness and mitigate health risks.

It has been determined, however, that self-reported questionnaires are consistently subject to reliability issues over time. As such, the inventors have realized that the use of the self-assessment HRA as a system for obtaining the necessary data to analyze health risks may be problematic. In contrast, embodiments of the present invention provide a novel approach in which real-time biometric monitoring and 3D visualizations may be provided in real time without relying (either entirely or at least partially) on the existing self-reported questionnaire model of HRAs.

The cybernetics information system 100 can provide data visualization and positive/negative reinforcement for a large number (for example thousands) of incoming streams of data which could not be obtained or processed using existing systems. In some embodiments, the cybernetics information system 100 is operable to track the user 10, in real-time, as the user 10 undertakes behavioral change. For example, such user tracking may utilize behavioral change models such as the Transtheoretical Model (TTM), Health Belief Model (HBM), Theory of Planned Behavior (TPB), and Social Cognitive Theory (SCT), for example. Alerts and prompts may be sent to the user and/or a training facilitator (or employer, etc.) based on which stage of the TTM the user currently resides, for example preparation, contemplation, relapse, etc.

TTM is one of a number of commonly referred to health behavior change theoretical constructs, together with the HBM, TPB, and SCT. The TTM was developed through studies examining the experiences of smokers to try to understand why some individuals require external assistance to quit while others are capable of quitting without external assistance. The TTM focuses on temporal consideration within the decision-making of the individual, concluding that a deciding factor was a "readiness" of the individual to quit smoking. The TTM models intentional change as a cycle based upon readiness. The TTM is based upon an assumption that individuals do not change behaviors quickly and decisively. Rather, change in behavior, especially habitual behavior, occurs continuously through a cyclical deterministic process.

Figure 10:
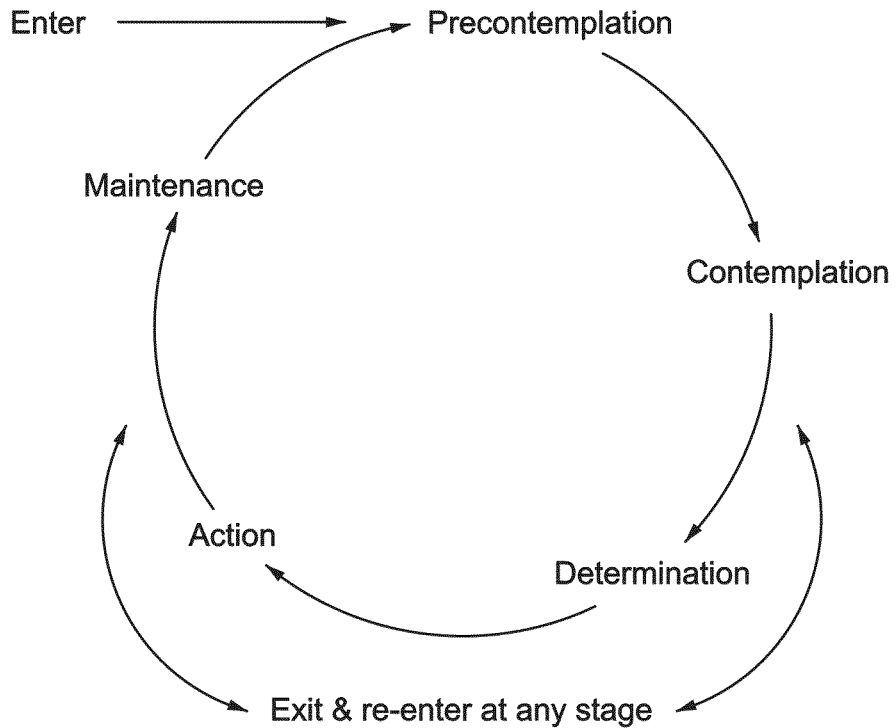
FIG. 10 is an illustration of the Transtheoretical Model.

The TTM is illustrated in FIG. 10. The TTM allows for integration of various other different behavioral theories and constructs, which can be applied to various stages of the model where these behavior theories may be most effective. For example, the TTM is mutually inclusive of HBM, TPB and SCT. Referring to FIG. 10 The TTM posits that individuals and populations move through a number of stages of change: "precontemplation", "contemplation", "determination", "action", "relapse", and "maintenance". For each stage of change within the TTM model, different intervention strategies are most effective at moving the individual to the next stage of change and subsequently through the model to maintenance, the ideal stage of behavior.

Pre-contemplation: Throughout this stage, individuals do not intend to take any action towards a given behavior in "the foreseeable future" (for example, within the next six months). Individuals are often unaware or even in denial that their current behavior is problematic or produces negative consequences. Individuals in this stage often underestimate the benefits of changing behavior and place too much emphasis on the costs. The cost/benefit analysis may be referred to as the "decisional balance". It is at this stage that the decisional balance weighted toward the "costs" of behavior change.

Contemplation: Throughout this stage, individuals are intending to start the healthy behavior within the foreseeable future (for example within the next six months). Individuals recognize and accept that their behavior may be problematic, and a more thoughtful and practical consideration of the decisional balance of the benefits and costs of changing behavior takes place, with equal emphasis placed on both the costs and benefits. Even with this recognition, individuals may still feel ambivalent toward changing their behavior. This ambivalence demonstrates a decisional balance is weighted evenly between both the costs and benefits of the change.

Determination: Throughout this stage, individuals are ready to take action (for example within the next thirty days). Individuals start to take small steps toward the behavior change, and believe that changing behavior can lead to a healthier life. It is at this stage that the decisional balance is weighted toward the benefits of the change.

Action: Throughout this stage, an individual has recently (for example, within the preceding six months) changed their behavior and intend to keep moving forward with that behavior change. Individuals may exhibit intent by modifying the problem behavior or acquiring new healthy behaviors. It is at this stage that the decisional balance is weighted toward the benefits of the change.

Maintenance: Throughout this stage, individuals have sustained their behavior change for some time (for example, longer than six months) and intend to maintain the behavior change. Individuals in this stage work to prevent relapse to earlier stages. It is often at this stage that individuals may reach a higher level of achievement in change behavior and become role models for others.

There are ten well-recognized processes of change that have been identified, where some of the ten processes are more relevant to a specific stage in the TTM than others of the ten processes. These processes result in strategies that help individuals make and maintain change. The ten processes of change are:

1. Consciousness Raising: Increasing awareness about the healthy behavior. Finding and learning new facts, ideas, and tips that support the health behavior change.
2. Dramatic Relief: Emotional arousal connected to the healthy behavior, whether positive or negative. For example, a negative emotional arousal may be connected with the unhealthy behavior (fear, anxiety, and worry, etc.).
3. Self-Reevaluation: Self reappraisal to realize the healthy behavior is part of who they want to be.
4. Environmental Reevaluation: This is a process of social reappraisal in which it is realized how an individual's unhealthy behavior may affect others.
5. Social Liberation: Environmental opportunities that exist to show society is supportive of the healthy behavior.
6. Self-Liberation: Commitment to change behavior based on the belief that achievement of the healthy behavior is possible.
7. Helping Relationships: Finding supportive relationships that encourage the desired change.
8. Counter-Conditioning: Replacing unhealthy behaviors and thoughts with healthy behavior and thoughts.
9. Reinforcement Management: Rewarding positive behavior and reducing the rewards that come from negative behavior.
10. Stimulus Control: Re-engineering an individual's environment to provide reminders and cues that support and encourage the healthy behavior and remove those that encourage the unhealthy behavior.

There are several limitations of TTM, which may be considered when using this theory in public health. The TTM does not generally give regard to the social context in which change occurs, such as situational, environment, and economic. One suggested deficiency of the TTM is that the parameters and lines between the stages can be arbitrary with no set criteria as to how to determine an individual's exact place (for example the stage) within the TTM. The questionnaires that have been developed and used to assign an individual to a stage of change are not always standardized or validated. The TTM does not provide a clear sense of how much time is needed for each stage, or how long an individual can remain in a stage. The TTM assumes that individuals make coherent and logical plans in their decision-making process when this is not always true. Nonetheless, however, the TTM can help to provide useful strategies for health interventions to address individuals at various stages of a decision-making process. The suggested interventions may be tailored (i.e., a message or programme component specifically created for a target population's level of knowledge and motivation) and effective. The TTM encourages an assessment of an individual's current stage of change and accounts for relapse in individual's decision-making process. The cybernetics information system 100 of the present system may be used to aid in a determination as to where in the TTM the user 10 is currently placed and to help provide effective motivational and instructional visualizations.

Figure 11:
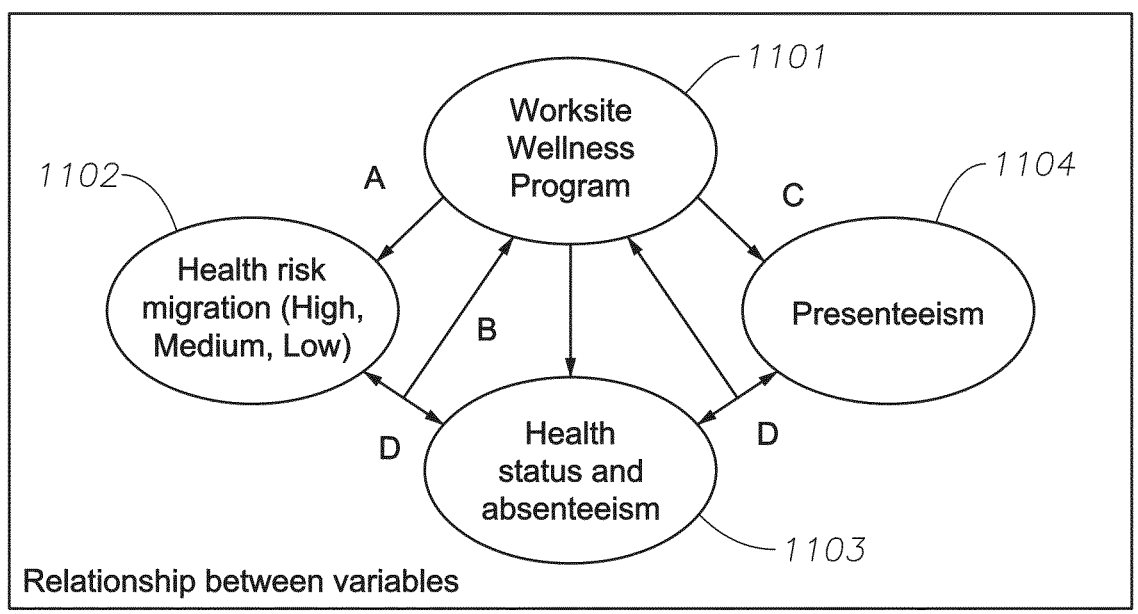
FIG. 11 is a schematic illustration of relationships between variables impacting a worksite wellness program.

FIG. 11 illustrates a map 1100 depicting the effects of an organizational (for example worksite) wellness program 1101 on three interrelated factors: health risk migration 1102, health status and absenteeism 1103 and presenteeism 1104. A relationship between the wellness program 1101 and health risk migration 1102 is shown by a connection A, a relationship between the wellness program 1101 and health status and absenteeism 1103 is shown by a connection B and a relationship between the wellness program 1101 and presenteeism 1104 is shown by a connection C. A relationship between the factors 1102, 1103, 1104 is depicted by connections D therebetween.

Using data gathered during two wellness program cohort studies available from the Health Enhancement Research Organization (HERO), the inventors have formulated an equation for measuring cost reductions that may be obtained through reducing presenteeism 1104 through a wellness program 1101. A first cohort study (with 1157 participants) operated between 2005 and 2011 to examine changes to a number of employee health risk factors as a result of enrolment within a wellness program. Table 1 below, sets out a number of findings from the first cohort study.

TABLE 1

| Variables | Pre Test (n = 1157) | | Post Test (n = 1157) | |
| --- | --- | --- | --- | --- |
| | No. | % | No. | % |
| a. BMI | | | | |
| 1. Low | 11 | 1.0 | 13 | 1.1 |
| 2. Normal | 355 | 30.7 | 374 | 32.3 |
| 3. Over weight | 486 | 42.0 | 535 | 46.2 |
| 4. Obese | 283 | 24.5 | 223 | 19.3 |
| 5. Severely Obese | 22 | 1.9 | 12 | 1.0 |
| b. BMR | | | | |
| 1. Warning | 8 | 0.8 | 12 | 1.2 |
| 2. Low Energy | 84 | 8.5 | 89 | 9.0 |
| 3. Below Average | 220 | 22.2 | 233 | 23.6 |
| 4. Average energy | 374 | 37.8 | 371 | 37.5 |
| 5. High Energy | 302 | 30.5 | 284 | 28.7 |

TABLE 1-continued

| | Pre Test (n = 1157) | | Post Test (n = 1157) | |
|---|---|---|---|---|
| Variables | No. | % | No. | % |
| 6. Extreme Energy | 0 | 0.0 | 0 | 0.0 |
| c. FAT | | | | |
| 1. Essential Fat | 1 | 0.1 | 2 | 0.2 |
| 2. Athlete Level | 40 | 4.7 | 46 | 5.4 |
| 3. Optimal Level | 221 | 26.2 | 220 | 26.0 |
| 4. Moderate Excess of fat | 477 | 56.4 | 469 | 55.5 |
| 5. Maximum excess of fat | 106 | 12.5 | 108 | 12.8 |
| d. Blood Pressure | | | | |
| 1. Low BP | 88 | 9.2 | 109 | 11.4 |
| 2. normal BP | 589 | 61.5 | 736 | 76.9 |
| 3. High BP | 280 | 29.3 | 112 | 11.7 |
| e. Active Level | | | | |
| 1. Standard | 1125 | 97.3 | 1118 | 96.6 |
| 2. Athletic | 26 | 2.2 | 34 | 2.9 |

The second of the two cohort studies considered a number of 6366 participants between 2007 and 2009. A sample of results of the second cohort study is provided in Table 2.

TABLE 2

| | Mean Value | |
|---|---|---|
| Variables | Pre Test | Post Test |
| Weight | 80.07 | 77.91 |
| BMI | 27.52 | 26.91 |
| BMR | 1995.17 | 1785.83 |
| Fat % | 25.88 | 25.51 |
| Fat Mass | 21.31 | 20.81 |
| FFM Kg | 58.56 | 57.74 |
| Systolic BP | 130.12 | 124.17 |
| Diastolic BP | 77.29 | 74.88 |

The research methodology of the two cohort studies has aided in the development of the presenteeism equation described below. The inventors considered both cohort studies together to model the effect of the two wellness programs concerned (i.e. the wellness programs at issue in each of the first and second cohort studies) to evaluate the relative health risk transitions (relationship A in FIG. 11) that resulted from the wellness interventions. A health risk migration is when, for example, a health risk migrates from one category of health risk to another. For example, over the course of each study a health risk for an individual may migrate from a high to a medium to a low health risk category. By modelling the relationships A, B using the data from the two cohort studies, the healthcare costs saved (cost avoidance) due to the reduced relative risks and disease prevention was ascertained. The cost avoidance data is based on excess risk premium cost data applied by the health insurance industry. Insurance premium data is available, for example, through the Mercer Employer Health Surveys.

Figure 12:
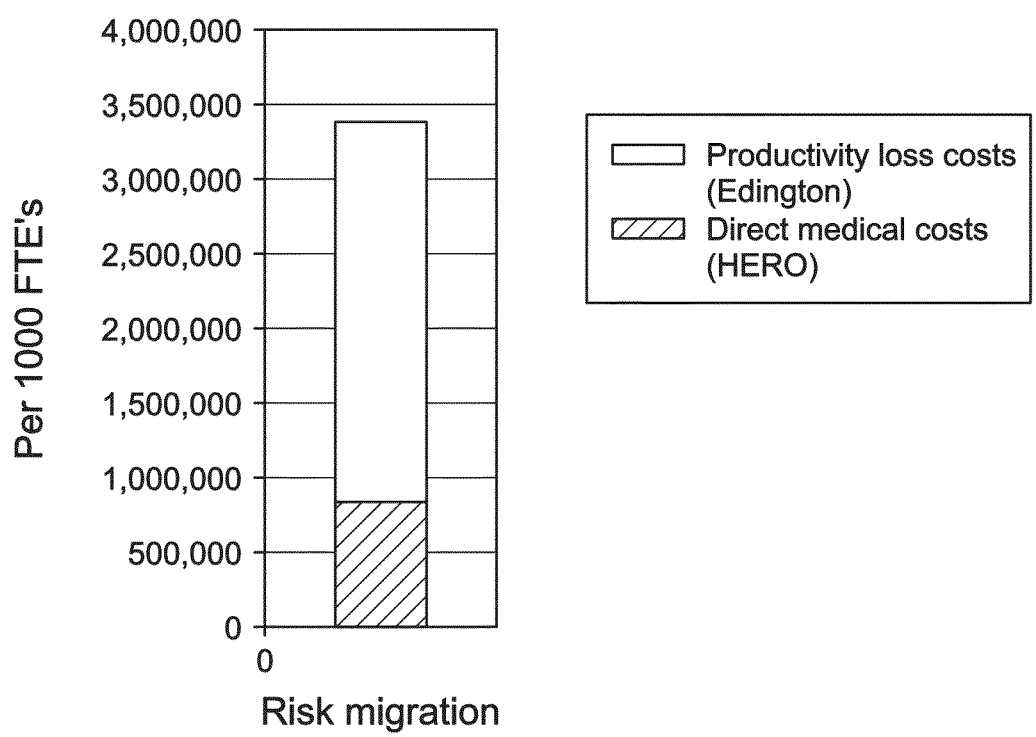
FIG. 12 is a chart showing benefits of workplace wellness programs.
Figure 13:
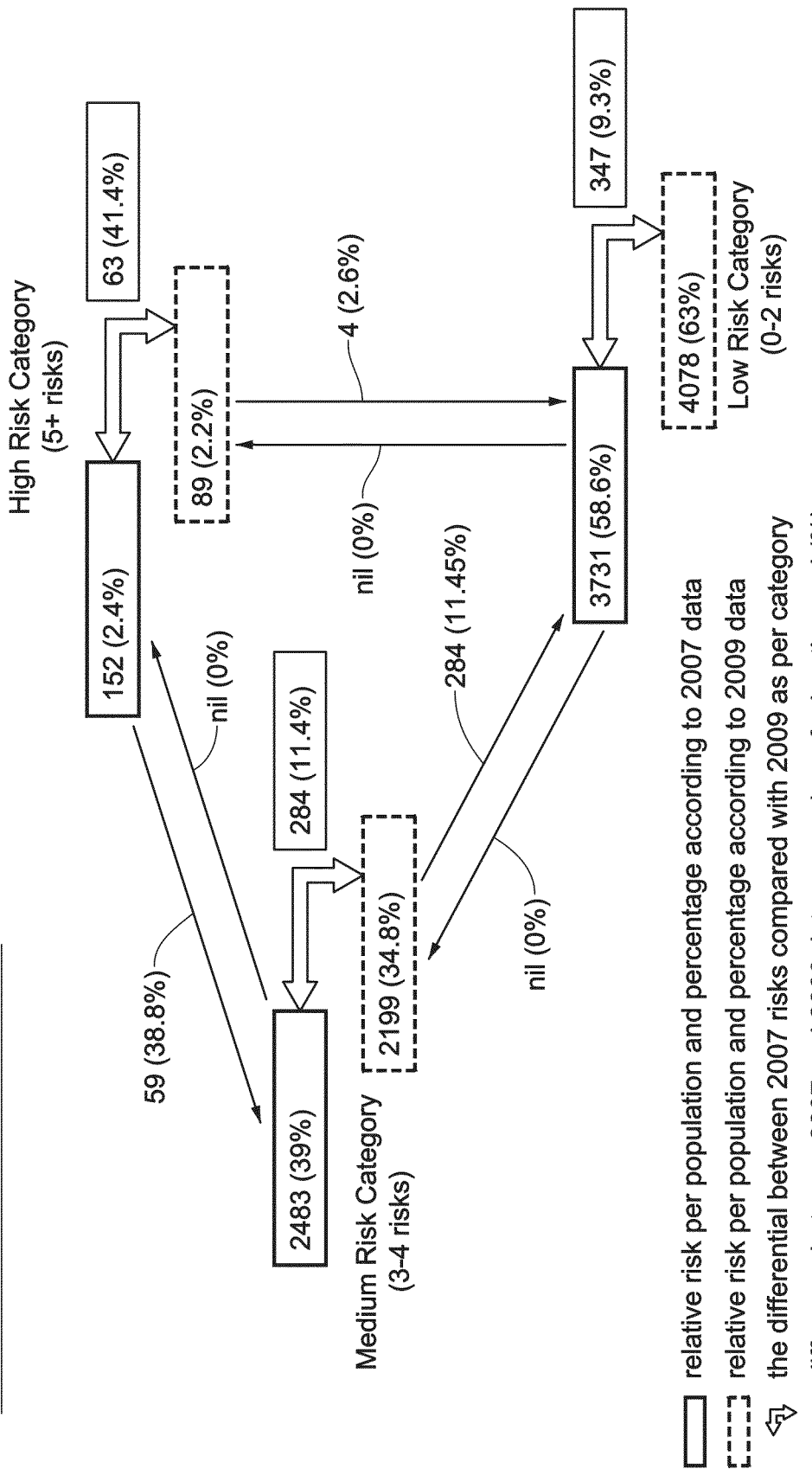
FIGS. 13 and 14 schematically illustrate migrations of risk categories observed in respective studies of workplace wellness programs.
Figure 14:
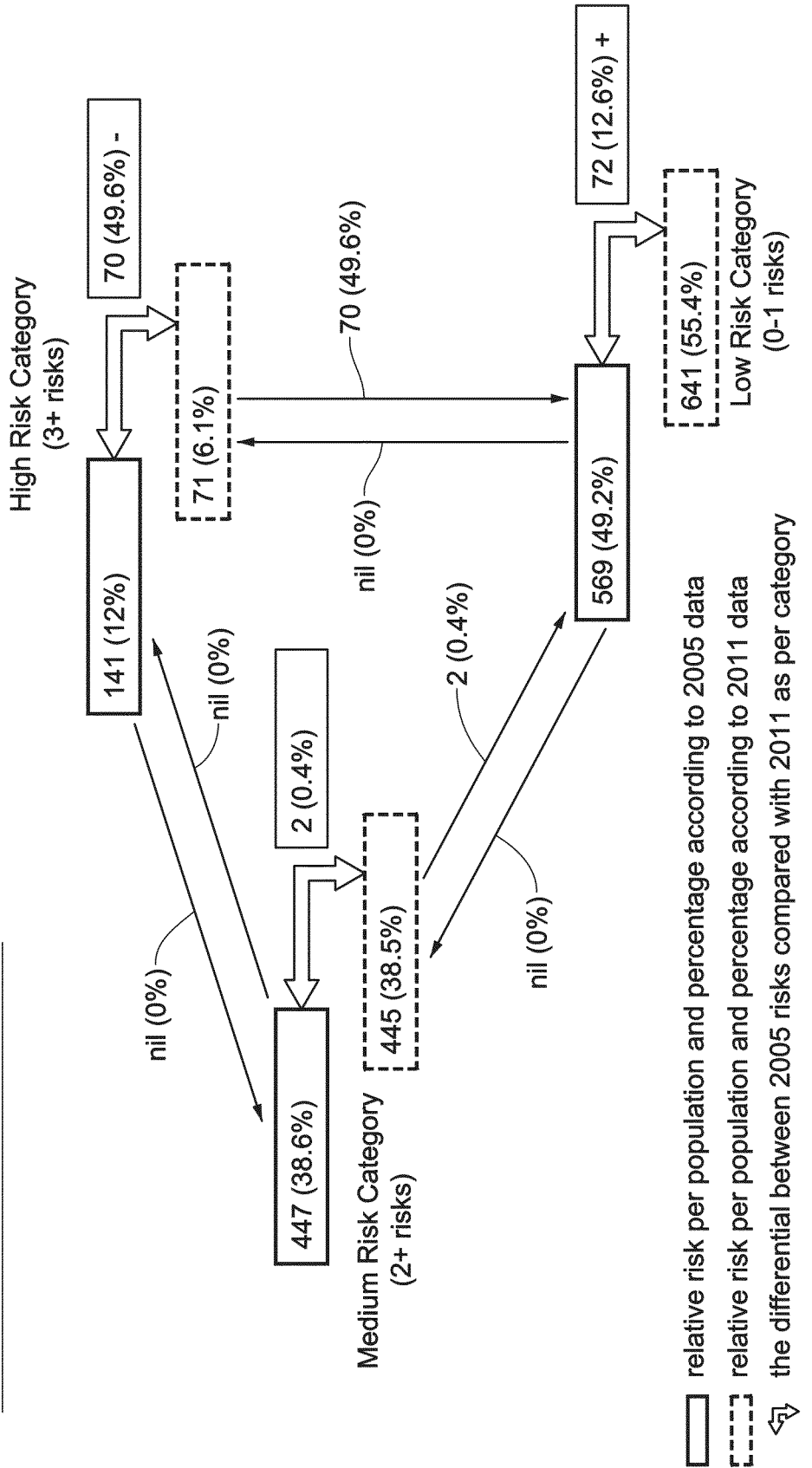

Having established a greater understanding of the A relationship (FIG. 11), the inventors also examined the relationship B of the wellness programs on the total medical cost avoidance, which is considered to follow from the effect on the health status of the individual. It has been determined that across the two cohort studies, a total medical cost avoidance of $8,874,277 was achieved for a total of 7523 employees. FIG. 12 illustrates costs saved as a result of reducing productivity loss and direct medical costs as a ratio per 1000 Full Time Equivalent (FTE) employees. It can be seen from FIG. 12 that the two cohort studies indicate that the two wellness programs resulted a total of almost $3500 cost savings per 1000 FTE employees.

To arrive at a presenteeism equation, the population data for each of the two cohort studies described above were normalized for the difference in years over which the cohort studies were conducted. The average risks α1 avoided per employee per year, over the first study and the average number of risks α2 avoided per employee per year over the second study, may be determined according to equations (1a), (1b) respectively, $$\alpha_1 = \frac{\Delta P_{H1} R_{H1} + \Delta P_{M1} R_{M1} + \Delta P_{L1} R_{L1}}{\Delta t1} \quad (1a)$$

$$\alpha_2 = \frac{\Delta P_{H2} R_{H2} + \Delta P_{M2} R_{M2} + \Delta P_{L2} R_{L2}}{\Delta t2} \quad (1b)$$

where $\Delta t1$ is the number of years between the start and end of the first study, $R_{H1}$, $R_{M1}$, and $R_{L1}$, are the average number of risks associated with the high, medium and low risk categories respectively and $\Delta P_{H1}$, $\Delta P_{M1}$, and $\Delta P_{L1}$ are the percentages of population migrations occurring over the first study in the high, medium, and low risk categories respectively. In some embodiments, the average number of risks for a category can be predetermined. For example, the high, medium and low risk categories may be associated with 5, 3 and 0 risks, respectively. The number of risks for a category may be based on historical heath data for one or more population groups, for example. In some embodiments, $\Delta P_{H1}$ indicates a change in the percentage of the study population that is classified as high risk between the start and end of the first study. $\Delta t2$ is the number of years between the start and end of the second study, $R_{H2}$, $R_{M2}$, and $R_{L2}$, are the average number of risks associated with the high, medium and low risk populations, respectively, of the second study, and $\Delta P_{H2}$, $\Delta P_{M2}$, and $\Delta P_{L2}$ are the percentages of population migrations occurring over the second study in the high, medium, and low risk categories, respectively.

Given equations (1a) and (1b), the average number of risks avoided per employee per year α over the two studies may be given by, $$\alpha = \frac{\alpha_1 + \alpha_2}{2} \quad (2)$$

Given a number of employees impacted by the wellness program, ψ, the average number of risks avoided per year ΔΓ may be given by, $$\Delta\Gamma = \alpha\psi \quad (3)$$

The average medical cost avoided per year as a result of the wellness program, Δζ, may be given by, $$\Delta\zeta_d = \Gamma\mu \quad (4)$$

where μ is the average medical cost per risk.

Indirect costs avoided per year $\Delta\zeta_i$ may be a ratio to direct costs $\Delta\zeta_d$. For example, referring again to FIG. 12, in the two cohort studies discussed herein, approximately $3.7 USD of indirect costs were saved for every $1 USD of direct costs. It will be appreciated that the value of indirect costs saved may vary in dependence upon a number of factors. The average total costs saved ΔC as a result of a wellness program, may be given by, $$\Delta C = \Delta\zeta_d + \Delta\zeta_i \quad (5)$$

Figure 15:
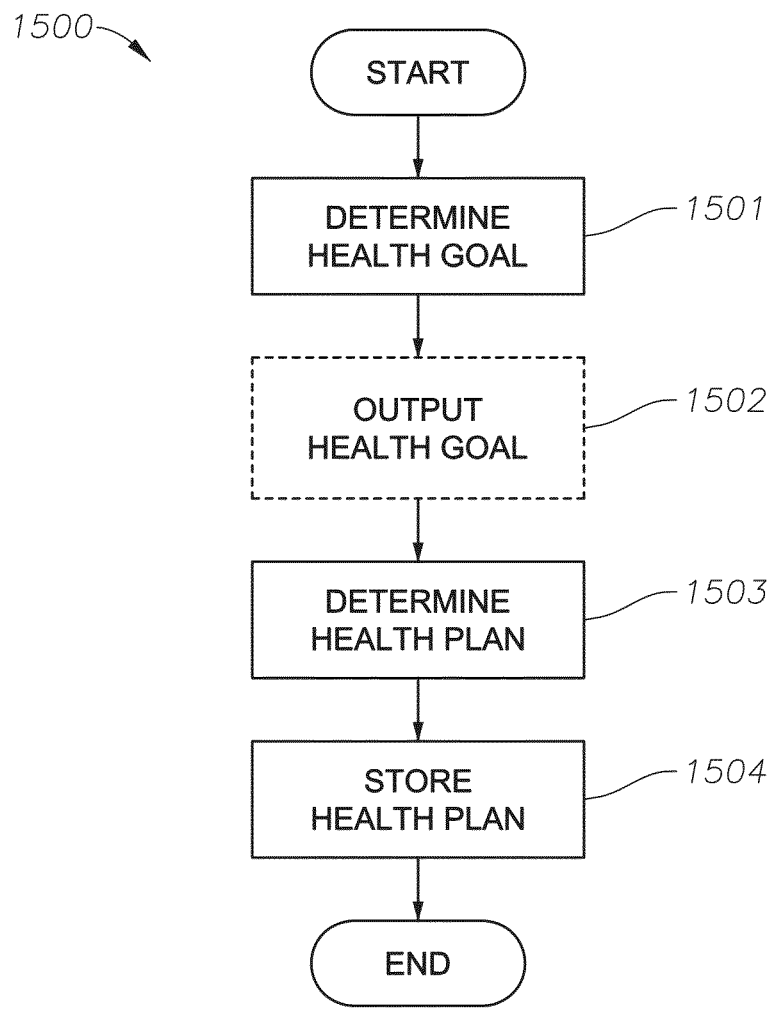
FIG. 15 is a flowchart illustrating processing that may be performed to provide a health plan in accordance with an embodiment of the invention.
Figure 16:
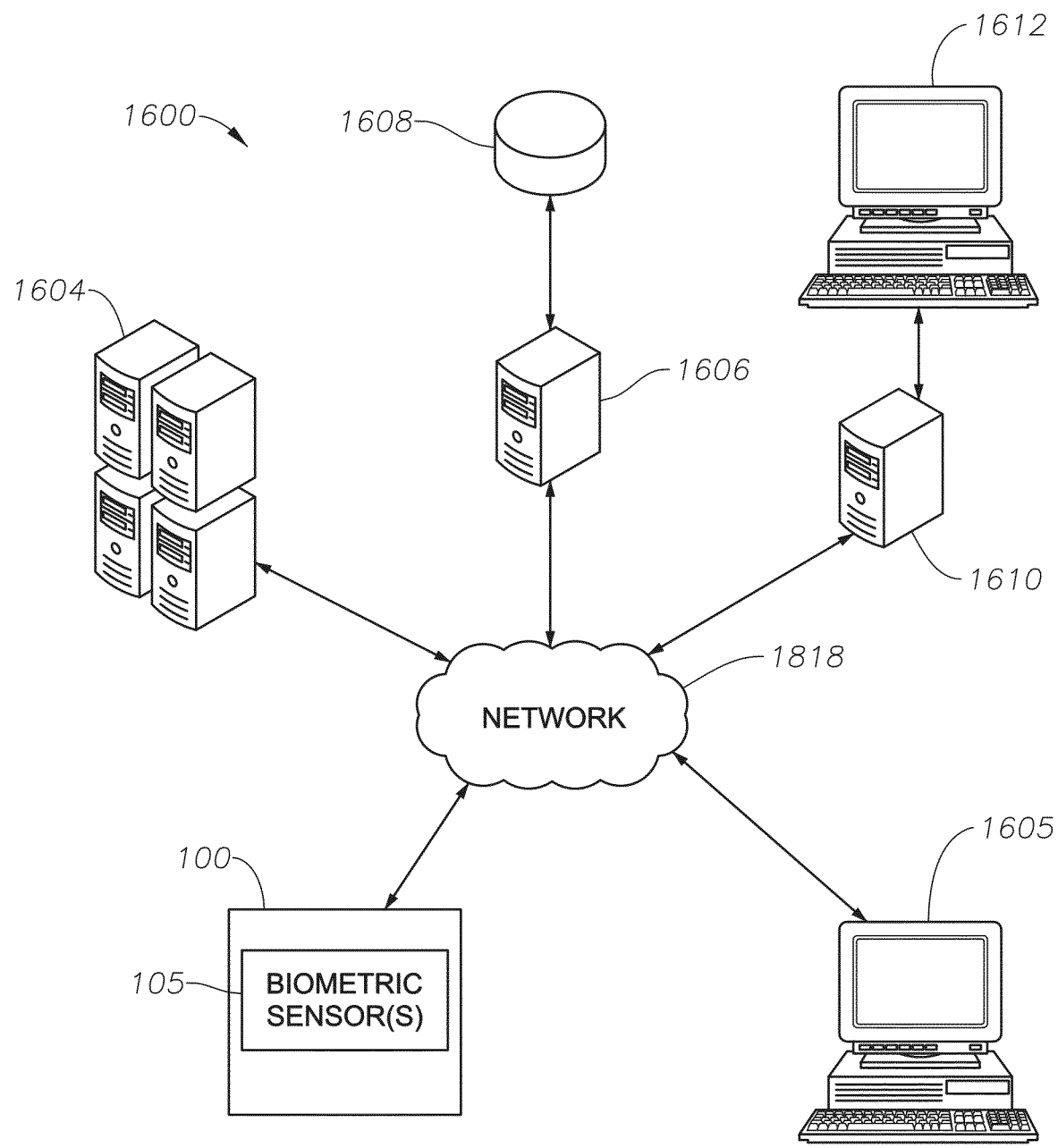
FIG. 16 is a schematic illustration of an arrangement of networked components according to an embodiment of the invention.

Referring to FIGS. 15 and 16, these illustrate health risk migrations observed in the first and second cohort studies respectively. Using the numbers obtained in the two cohort studies in equations (1) to (5) above, together with the ration of 3.7:1 of indirect costs saved to direct costs saved, it may be determined that the total costs saved per year ΔC across the wellness programs of the two studies is of the order of $3.425 million.

Based on the above, the inventors have determined the formula (6) for incurred cost, $$C = C_T \times \mu \times \psi \times (P_L R_L + P_M R_M + P_R R_H) \tag{6}$$

and the formula (7) for cost avoidance due to medical risks, $$\frac{dC}{dt} = C_T \times \mu \times \psi \times \left( \frac{dP_L}{dt} R_L + \frac{dP_M}{dt} R_M + \frac{dP_H}{dt} R_H \right) \tag{7}$$

where $C_T$ is the total cost saved. Continuing with the above example, $C_T$ may be $4.7, where $3.7 USD of indirect costs are saved for every $1 USD of direct costs. The cost, C, may represent the total cost attributed to risks for the population. The cost avoidance, $$\frac{dC}{dt},$$

may represent the change in cost (e.g., a savings of increase) attributable to a change (e.g., reduction or increase) in risk over the associated period of time.

In addition, the above equations may be aligned with a particular field. For example, the above equations may be aligned to the oil and gas industry by relating cost avoidance and productivity loss avoidance with market value and production value of barrels of oil. For example, taking again the example of the two cohort studies, assuming market value of a barrel of oil is $107/barrel, the savings in costs through reduction in presenteeism may translate to 32009 barrels of oil/year.

The cybernetics information system 100, providing 3D visualization bio-feedback therefore provides an effective tool to reduce societal cost of injury and disease through empowering effective health behavior change, and prevent human pain and suffering. Depth perception has been indicated to be a major factor attributed to how an experience is perceived in the mind of a user, and the provision of 3D visualization biofeedback provides for experiences that are more readily retained. Statistical analysis has demonstrates associations between lifestyle risk factors such as smoking, physical inactivity with blood pressure, blood sugar and body weight. It has been documented that while brains can store words, stories and two-dimensional (2D) images as data for re-collection, such stored data tends to be rationally and consciously manipulated by the brain with a potentially different outcome based on the situation. Stored data does not seem to subconsciously affect behavior. Many learning retention studies have suggested a 7- to 8-fold increase in learning retention when a person experiences something first hand in comparison to only reading about it. Studies have found that on average, attending a live lecture only results in a 5% learning retention, while reading the same materials allows for twice as much learning retention (10%), viewing a multimedia version story-style version of the same materials results in a 25% learning retention, with learning retention reaching 75% when the person experiences things first hand. Depth perception is a primary differentiating factor attributed to an "experience".

In some embodiments, the biometric data obtained from the cybernetics information system 100 may be used to provide the user 10 and/or a training provider, employer, etc., with a real-time and/or historic view (for example in an information dashboard displayed on the display 106 or on a display of another device) indicating one or more of the biometric states of the user 10.

In some embodiments, the cybernetics information system 100 may be operable to detect when one or more of the biometric states exceeds a boundary condition. Upon determining that one or more of the biometric states has exceeded a boundary condition, assistive prompts (or alerts) may be provided to the user 10. In some embodiments, a prompt may be automatically generated and provided directly to the user 10. For example, where the biometric sensors 105 comprise one or more blood pressure sensors, upon determining that a blood pressure threshold been exceeded, a prompt may be provided to the user to seek assistance. In some embodiments upon determining that one or more of the biometric states has exceeded a boundary condition, prompts may also or alternatively be transmitted to a further entity, such as for example, an employer or an emergency service. For example, received biometric data may be compared with thresholds to determine if the biometric data indicates a current health hazard (for example an extremely high blood pressure). One or more emergency services may be automatically notified responsive to making a determination that received biometric data indicates a current health hazard.

In some embodiments, one or more of the biometric boundary conditions (for example, a maximum heart rate) may be pre-set. For example, a user's heart rate may be compared to a known safe or desirable heart rate or heart rate range. Similarly, responses by the cybernetics information system 100, such as particular prompts (or alerts) provided to the user 10 may be pre-set.

In some embodiments, one or more biometric boundary conditions, goals, and/or prompts to be provided to the user 10 may be dynamically determined. That is, by monitoring a user's interactions with the cybernetics information system 100 over time, the cybernetics information system 100 may automatically personalize the interaction provided to each individual user of the cybernetics information system 100. In some embodiments, processing to determine a biological age of the user 10 (for example processing similar or the same as that discussed above with reference to FIG. 5) may be used to generate one or more plans for improvements to the health and wellbeing of the user 10. FIG. 15 is a flowchart illustrating a method 1500 that may be carried out in some embodiments of the invention. It will be appreciated that in some embodiments, the method of FIG. 15 may be used in combination with methods such as that shown in processing of FIG. 5.

At step 1501 at least one health goal is determined for the user 10. For example, a health goal may be determined responsive to the biometric data received from the user 10 during the processing of FIG. 5. For example, where the biometric data received from the user 10 via the biometric sensors 105 indicate that the user's lungs are in poor health and it is determined that the user smokes, a health goal may be set for the user to stop or reduce smoking. In some embodiments, the at least one health goal may be determined responsive to a determined biological age of the user 10. For example, in some embodiments, a health goal may comprise a target health-adjusted relative age for one or more organs of the user 10. For example, where it is determined that a health-adjusted relative age of one of the user's organs is greater than the user's chronological age, a health goal of reducing the health-adjusted relative age of that organ may be determined at step 1501. In some embodiments, the health goal is output (for example through display via the display 106, or otherwise conveyed). In some embodiments, determination of a health goal to reduce a health-adjusted relative age of an organ may further comprise selecting one or more target ones of the base images 103 corresponding to the organ and the desired reduced health-adjusted relative age of that organ. The processing at step 1502 may comprise displaying the one or more target base images 103 to the user 10. In this way, 3D bio-feedback is provided to the user 10 to more effectively facilitate a change in behavior.

At step 1503, a health plan may be established. The health plan may comprises one or more follow-up sessions. For example, it may be determined that a user should be re-appraised using the cybernetics information system 100 on a weekly, monthly, bi-monthly, etc. basis. The health plan may further comprise the allocation of resources to assist the user 10 in effecting a change of behavior. For example, if the health goal is to improve lung health, and it is determined that the user smokes, resources (for example smoking cessation aids, counseling, etc.) may be allocated to the user 10. Allocation of resources may be implemented responsive to a determination as to costs which may be avoided if a health change is successfully effected. For example, a determination as to resource allocation may be made responsive to an indication of costs that may be saved in accordance with one or more of equations (1) to (7) set out above.

In some embodiments, determination of a health plan may comprise determining a stage of the TTM. For example, if it is determined that the user 10 is in a pre-contemplation or contemplation stage of the TTM, the determination of health plan at step 1503 may comprise allocating additional resources (for example more frequent counseling, appraisals, motivational aids) to the user, than if it is determined that the user is in an action phase of the TTM. In some embodiments, for example, the health plan may be processed in order to schedule one or more appointments with a lifestyle coach, an employer, or other third party. Further, the scheduling of appointments may take account, for example, of the determined stage of the TTM on which the user is placed.

It will be appreciated, however, that the generation of a health plan at step 1503 may be based upon other criteria not discussed herein and in general will be determined in dependence upon the particular one or more health goals determined at step 1501. At step 1504, the health plan may be stored. The health plan may be stored by updating the user's profile data stored in the database 102, for example.

In some embodiments, the cybernetics information system 100 may utilize other information about the user 10 to determine the one or more health goals and to determine a health plan. For example, where one or more health profiles/reports are available for the user 10 (such as, for example, described in U.S. patent application Ser. No. 13/540,300 filed on Jul. 2, 2012 and titled "SYSTEMS, COMPUTER MEDIUM AND COMPUTER-IMPLEMENTED METHODS FOR MONITORING HEALTH OF EMPLOYEES USING MOBILE DEVICES", and/or U.S. patent application Ser. No. 13/540,153 filed on Jul. 2, 2012 and titled "SYSTEMS AND METHOD TO MONITOR HEALTH OF EMPLOYEE WHEN POSITIONED IN ASSOCIATION WITH A WORKSTATION"), such health profiles/reports may be utilized in determining appropriate health goals, health plans, feedback prompts, etc. to be provided to the user.

Data recorded and stored by the cybernetics information system 100 (such as biometric data received from the biometric sensors 105, health goals, health plans, health-adjusted relative ages, etc.) may be made available to the user and/or to other entities (for example employers, wellness coaches, etc.). For example, the cybernetics information system 100 may comprise, or may be connected to, a network of other devices to allow information to be shared between a number of users.

FIG. 16 is a block diagram that illustrates an exemplary arrangement 1600 in accordance with one more embodiments of the present invention. As depicted, the arrangement 1600 may include one or more cybernetics information systems 100 such as those illustrated in FIGS. 1 to 3. The arrangement 1600 further comprises one or more workstations, such as workstation 1605. The workstation 1605 may be used, for example, for reviewing real-time and/or historical data collected by the cybernetics information systems 100. The workstation 1605 may be used by the user 10 and or another entity, such as an employer, a wellness coach, etc.

The arrangement 1600 further comprises one or more servers 1804 (of which one is depicted), one or more file servers 1606 (of which one is depicted) coupled to one or more databases 1608 (of which one is depicted), and one or more web servers 1610 (of which one is depicted) connected to one or more remote computers 1612 (of which one is depicted).

In some embodiments and as depicted, the entities of the training cybernetics information system 100 are communicatively coupled via a network 1818. Database 1608 may store health information 1809 (including for example, personal profile information, health profile information, collected user biometrics, organ specific health-adjusted relative ages, and/or the like) for one or more users. In some embodiments, the database 1608 may be, or may comprise part of, the one or more databases 102.

In some embodiments, the network 1818 includes an element or system that facilitates communications between entities of arrangement 1600. For example, the network 1818 may include an electronic communications network, such as the Internet, a local area network ("LAN"), a wide area ("WAN"), a wireless local area network ("WLAN") a cellular communications network or the like. In some embodiments, the network 1818 includes a single network or combination of networks. For example, the one or more cybernetics information systems 100, the workstation 1605, the server 1804, the file server 1606, and/or the web server 1610, may be networked using a private/LAN, with the remote computers 1612 (for example, user home computers, external service provider computer, emergency service computers, and/or the like) connected to the web server 1610 via a WAN.

Through a networked arrangement such as that depicted in FIG. 16, the cybernetics information system 100 may be operable to interface with existing health monitoring systems and processes in place within an organization. For example, the cybernetics information system 100 may be operable to interface into health monitoring systems and methods. In this way, for example, the techniques described herein may be used to together with systems, methods and apparatuses to allow employers (or other entities) to monitor the health of employees (or other users), for example via one or more health dashboards. The techniques described herein, may further be used together with systems, methods and apparatuses to provide coaching using, for example, avatar-based coaching systems. In some embodiments, therefore, the cybernetics information system 100 may provide a first system in a multi-system for improving health and wellbeing of employees.

For example, the techniques described herein may be used in combination with techniques described in U.S. patent application Ser. No. 13/540,300 filed on Jul. 2, 2012 and titled "SYSTEMS, COMPUTER MEDIUM AND COMPUTER-IMPLEMENTED METHODS FOR MONITORING HEALTH OF EMPLOYEES USING MOBILE DEVICES", U.S. patent application Ser. No. 13/540,153 filed on Jul. 2, 2012 and titled "SYSTEMS AND METHOD TO MONITOR HEALTH OF EMPLOYEE WHEN POSITIONED IN ASSOCIATION WITH A WORKSTATION", U.S. patent application Ser. No. 13/540,028 filed on Jul. 2, 2012 and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. patent application Ser. No. 13/540,067 filed on Jul. 2, 2012 and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,095 filed on Jul. 2, 2012 and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,124 filed on Jul. 2, 2012 and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,180 filed on Jul. 2, 2012 and titled "SYSTEMS, COMPUTER MEDIUM AND COMPUTER-IMPLEMENTED METHODS FOR MONITORING AND IMPROVING BIOMECHANICAL HEALTH OF EMPLOYEES", U.S. patent application Ser. No. 13/540,208 filed on Jul. 2, 2012 and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", U.S. patent application Ser. No. 13/540,335 filed on Jul. 2, 2012 and titled "SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY", U.S. patent application Ser. No. 13/540,374 filed on Jul. 2, 2012 and titled "SYSTEMS, COMPUTER MEDIUM AND COMPUTER-IMPLEMENTED METHODS FOR MONITORING HEALTH AND ERGONOMIC STATUS OF DRIVERS OF VEHICLES" (now U.S. Pat. No. 8,872,640), and/or U.S. patent application Ser. No. 13/540,262 filed on Jul. 2, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", the disclosures of which are incorporated herein by reference in their entireties.

In the various embodiments of the invention described herein, a person having ordinary skill in the art will recognize that various types of memory are readable by a computer, such as the memory described herein in reference to the various computers and servers, for example, computer, computer server, web server, or other computers with embodiments of the present invention. Examples of computer-readable media can include but are not limited to: nonvolatile, hard-coded type media, such as read only memories (ROMs), CD-ROMs, and DVD-ROMs, or erasable, electrically programmable read only memories (EEPROMs); recordable type media, such as floppy disks, hard disk drives, CD-R/RWs, DVD-RAMs, DVD-R/RWs, DVD+R/RWs, flash drives, memory sticks, and other newer types of memories; and transmission type media such as digital and analog communication links. For example, such media can include operating instructions, as well as instructions related to the systems and the method steps described above and can operate on a computer. It will be understood by those skilled in the art that such media can be at other locations instead of, or in addition to, the locations described to store computer program products, for example, including software thereon. It will be understood by those skilled in the art that the various software modules or electronic components described above can be implemented and maintained by electronic hardware, software, or a combination of the two, and that such embodiments are contemplated by embodiments of the present invention.

More generally, in the drawings and specification, there have been disclosed typical embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

In the drawings and specification, there have been disclosed embodiments of methods, systems, and non-transitory computer-readable medium having computer program stored therein of the present invention, and although specific terms are employed, the terms are used in a descriptive sense only and not for purposes of limitation. The embodiments of methods, systems, and non-transitory computer-readable medium having computer program stored therein of the present invention have been described in considerable detail with specific reference to these illustrated embodiments. It will be apparent, however, that various modifications and changes can be made within the spirit and scope of the embodiments of methods, systems, and non-transitory computer-readable medium having computer program stored therein of the present invention as described in the foregoing specification, and such modifications and changes are to be considered equivalents and part of this disclosure.

In this patent, certain U.S. patents, U.S. patent applications, or other materials (for example, articles) have been incorporated by reference. The text of such U.S. patents, U.S. patent applications, and other materials is, however, only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference in this patent.

That claimed is:

1. A device to provide three-dimensional (3D) depictions of health of human organs of a user relative to the user's age based on sensed biometrics of the user, the device comprising:
   one or more processors;
   one or more databases in communication with the one or more processors and having a plurality of three-dimensional (3D) depictions of each of one or more human lungs stored therein, the plurality of 3D depictions of each of the one or more human lungs thereby define a set of base images of the respective human lung, each set of base images configured to include a plurality of base images of the respective human lung at each of a plurality of different ages, the plurality of base images of the respective human lung at each of the plurality of different ages configured to include one or more depictions of the respective human lung at the respective different age at each of a plurality of health levels among a range of health levels, each of the plurality of health levels configured to indicate health risk;

one or more input and output units in communication with the one or more processors and positioned to receive input and output communication;

one or more biometric sensors in communication with the one or more processors and configured to sense biometric parameters of a user, the user having a chronological age;

one or more displays in communication with the one or more processors and configured to display an electronic user interface thereon; and non-transitory memory medium in communication with the one or more processors, the memory medium including computer-readable instructions stored therein that when executed cause the one or more processors to perform the operations of:

selecting, for each of the one or more human lungs and responsive to the one or more input and output units, a first base image of the set of base images of the respective human lung that approximates a depiction of the respective human lung at the user's chronological age at a preselected one of the plurality of health levels from the one or more databases, receiving one or more biometric parameters of the user through the one or more biometric sensors to generate a plurality of biometric measurements for each of the one or more biometric parameters, each of the one or more biometric parameters associated with one of the one or more human lungs, converting the plurality of biometric measurements for each of the one or more biometric parameters into electronic biometric data, determining a health-adjusted relative age of each of the one or more human lungs of the user responsive to analysis of the electronic biometric data, the health-adjusted relative age configured to indicate health level of the respective human lung of the user relative to the user's age, selecting, for each of the one or more human lungs, a second base image of the set of base images of the respective human lung that approximates a depiction of the respective human lung at the determined health-adjusted relative age of the respective human lung from the one or more databases, and displaying, by the electronic user interface and for a selected one or more of the one or more human lungs, the first base image and the second base image thereby to enable comparison of the determined health-adjusted relative age of the respective human lung and the user's age to indicate health of the respective human lung of the user visually.

2. The device as defined in claim 1, wherein selecting, for each of the one or more human lungs, a second base image is further responsive to the user's chronological age.

3. The device as defined in claim 1, wherein the one or more biometric sensors include a peak flow respiratory rate sensor, and wherein the electronic biometric data includes electronic lung data.

4. The device as defined in claim 3, wherein the device further includes a kiosk, and wherein at least one of the one or more displays and at least one of the one or more biometric sensors are positioned within the kiosk.

5. The device as defined in claim 1, wherein the one or more databases further include a plurality of health risk profiles, each of the plurality of health risk profiles associated with one or more of the plurality of health levels.

6. The device as defined in claim 1, wherein the set of base images of each respective human lung comprises a hierarchical structure having a plurality of levels, each of the plurality of levels associated with one or more user characteristics, the plurality of levels configured to include at least a gender level, a height level and an age level.

7. A device to provide three-dimensional (3D) depictions of health of human lungs of a user relative to the user's age based on sensed biometrics of the user, the device comprising:

one or more processors;

one or more databases in communication with the one or more processors and having a plurality of preselected three-dimensional (3D) depictions of each of one or more human lungs stored therein, the plurality of 3D depictions of each of the one or more human lungs define a set of base images of the respective human lung, each set of base images configured to include a plurality of base images of the respective human lung at each of a plurality of different ages, the plurality of base images of the respective human lung at each of the plurality of different ages configured to include one or more depictions of the respective human lung at the respective different age at each of a plurality of health levels among a range of health levels, each of the plurality of health levels configured to indicate health risk;

one or more input and output units in communication with the one or more processors and positioned to receive input and output communication; and non-transitory memory medium in communication with the one or more processors, the memory medium including computer-readable instructions stored therein that when executed cause the one or more processors to perform the operations of:

selecting, for each of the one or more human lungs and responsive to the one or more input and output units, a first base image of the set of base images of the respective human lung that approximates a depiction of the respective human lung at a user's age at a preselected one of the plurality of health levels from the one or more databases, sensing one or more biometric parameters of the user by use of one or more biometric sensors in communication with the one or more input and output units to generate a plurality of biometric measurements for each of the one or more biometric parameters, each of the one or more biometric parameters associated with one of the one or more human lungs, converting the plurality of biometric measurements for each of the one or more biometric parameters into electronic biometric data, determining a health-adjusted relative age of each of the one or more human lungs of the user responsive to analysis of the electronic biometric data, the health-adjusted relative age configured to indicate health level of the respective human lung of the user relative to the user's age, selecting, for each of the one or more human lungs, a second base image of the set of base images of the respective human lung that approximates a depiction of the respective human lung at the determined health-adjusted relative age of the respective human lung from the one or more databases, and displaying, by an electronic user interface and for a selected one or more of the one or more human lungs responsive to the one or more input and output units, the first base image and the second base image thereby to enable comparison of the determined health-adjusted relative age of the respective human lung and the user's age to indicate health of the respective human lung of the user visually.

8. The device as defined in claim 7, wherein displaying the first base image and the second base image includes display of the first base image and the second base image in a relatively side-by-side relationship.

9. The device as defined in claim 7, wherein the electronic biometric data includes electronic lung data.

10. The device as defined in claim 7, wherein the one or more databases further include a plurality of health risk profiles, each of the plurality of health risk profiles associated with one or more of the plurality of health levels.

11. A method to provide three-dimensional (3D) depictions of health of human lungs of a user relative to the user's age based on sensed biometrics of the user, the method comprising:

selecting, for each of one or more human lungs, one of a plurality of preselected three-dimensional (3D) depictions of the respective human lung that approximates a depiction of the respective human lung at the user's age at a preselected one of the plurality of health levels, the plurality of 3D depictions of each of the one or more human lungs thereby to define a set of base images of the respective human lung, each set of base images configured to include a plurality of base images of the respective human lung at each of a plurality of different ages, the plurality of base images of the respective human lung at each of the plurality of different ages configured to include one or more depictions of the respective human lung at the respective different age at each of a plurality of health levels among a range of health levels, each of the plurality of health levels configured to indicate health risk, the selected one of set of base images of the respective human lung thereby to define a first base image;

sensing one or more biometric parameters of a user by use of one or more biometric sensors to generate a plurality of biometric measurements for each of the one or more biometric parameters, each of the one or more biometric parameters associated with one of the one or more human lungs;

converting the plurality of biometric measurements for each of the one or more biometric parameters into electronic biometric data;

determining a health-adjusted relative age of each of the one or more human lungs of the user responsive to analysis of the electronic biometric data, the health-adjusted relative age configured to indicate health level of the respective human lung of the user relative to the user's age;

selecting, for each of the one or more human lungs, a second base image of the set of base images of the respective human lung that approximates a depiction of the respective human lung at the determined health-adjusted relative age of the respective human lung; and displaying, for a selected one or more of the one or more human lungs, the first base image and the second base image thereby to enable comparison of the determined health-adjusted relative age of the respective human lung and the user's age to indicate health of the respective human lung of the user visually.

12. The method as defined in claim 11, wherein displaying the first base image and the second base image includes display of the first base image and the second base image in a relatively side-by-side relationship.

13. The method as defined in claim 11, wherein the electronic biometric data includes electronic lung data.

14. The method as defined in claim 11, wherein each of a plurality of health risk profiles is associated with one or more of the plurality of health levels.

15. Non-transitory computer-readable medium having one or more computer programs stored therein operable by one or more processors to provide three-dimensional (3D) depictions of health of human lungs of a user relative to the user's age based on sensed biometrics of the user, the one or more computer programs configured to include a set of instructions that, when executed by the one or more processors, cause the one or more processors to perform the operations of:

selecting, for each of one or more human lungs, one of a plurality of preselected three-dimensional (3D) depictions of the respective human lung that approximates a depiction of the respective human lung at the user's age at a preselected one of the plurality of health levels, the plurality of 3D depictions of each of the one or more human lungs thereby to define a set of base images of the respective human lung, each set of base images configured to include a plurality of base images of the respective human lung at each of a plurality of different ages, the plurality of base images of the respective human lung at each of the plurality of different ages configured to include one or more depictions of the respective human lung at the respective different age at each of a plurality of health levels among a range of health levels, each of the plurality of health levels configured to indicate health risk, the selected one of set of base images of the respective human lung thereby to define a first base image;

sensing one or more biometric parameters of a user by use of one or more biometric sensors to generate a plurality of biometric measurements for each of the one or more biometric parameters, each of the one or more biometric parameters associated with one of the one or more human lungs;

converting the plurality of biometric measurements for each of the one or more biometric parameters into electronic biometric data;

determining a health-adjusted relative age of each of the one or more human lungs of the user responsive to analysis of the electronic biometric data, the health-adjusted relative age configured to indicate health level of the respective human lung of the user relative to the user's age;

selecting, for each of the one or more human lungs, a second base image of the set of base images of the respective human lung that approximates a depiction of the respective human lung at the determined health-adjusted relative age of the respective human lung; and displaying, for a selected one or more of the one or more human lungs, the first base image and the second base image thereby to enable comparison of the determined health-adjusted relative age of the respective human lung and the user's age to indicate health of the respective human lung of the user visually.

16. The medium as defined in claim 15, wherein displaying the first base image and the second base image includes display of the first base image and the second base image in a relatively side-by-side relationship.

17. The medium as defined in claim 15, wherein the electronic biometric data includes electronic lung data.

18. The medium as defined in claim 15, wherein comparison of the determined health-adjusted relative age of the respective human lung and the user's age indicates health risk of the user associated with the respective human lung, and wherein each of a plurality of health risk profiles is associated with one or more of the plurality of health levels.

19. The medium as defined in claim 18, wherein the operations further include:
  determining a health plan responsive to display of the first base image and the second base image for each of the one or more human lungs;
  updating a plurality of biometric data of a cohort group associated with a workplace wellness program thereby to define workplace wellness data responsive to analysis of the determined health-adjusted relative age of each of the one or more human lungs of the user; and
  scheduling a follow-up wellness appointment for the user with a lifestyle coach thereby to enhance adherence to the determined health plan.

* * * * *